(12) United States Patent
Zhang et al.

(10) Patent No.: US 9,244,035 B2
(45) Date of Patent: Jan. 26, 2016

(54) SALIVA GLUCOSE MONITORING SYSTEM

(71) Applicant: Northeastern University, Boston, MA (US)

(72) Inventors: Wenjun Zhang, Malden, MA (US); Ming L. Wang, Stoneham, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 14/153,647

(22) Filed: Jan. 13, 2014

(65) Prior Publication Data

US 2014/0197042 A1    Jul. 17, 2014

Related U.S. Application Data

(60) Provisional application No. 61/751,451, filed on Jan. 11, 2013, provisional application No. 61/860,519, filed on Jul. 31, 2013.

(51) Int. Cl.
G01N 27/327    (2006.01)

(52) U.S. Cl.
CPC .................................. *G01N 27/3271* (2013.01)

(58) Field of Classification Search
CPC . G01N 27/327; G01N 27/3272; G01N 27/48; G01N 27/26; G01N 33/487; G01N 33/48707; G01N 33/66; C12Q 1/00; C12Q 1/006; C12Q 1/54
See application file for complete search history.

(56) References Cited

U.S. PATENT DOCUMENTS

| | | | |
|---|---|---|---|
| 2007/0043283 A1* | 2/2007 | Cohan et al. | 600/345 |
| 2007/0208243 A1* | 9/2007 | Gabriel et al. | 600/347 |
| 2008/0029390 A1 | 2/2008 | Roche et al. | |
| 2009/0045055 A1 | 2/2009 | Rhodes et al. | |
| 2009/0095625 A1* | 4/2009 | Forrow | 204/403.14 |
| 2010/0072062 A1* | 3/2010 | Curry | 204/403.11 |
| 2011/0082356 A1* | 4/2011 | Yang et al. | 600/345 |
| 2014/0183059 A1* | 7/2014 | Whitesides et al. | 205/775 |

FOREIGN PATENT DOCUMENTS

WO    WO2012075331 A2    6/2012

OTHER PUBLICATIONS

Kang et al., Anal Biochem, 2007, 369,71-79.*
Wu, B.-Y., et al. "Amperometric glucose biosensor based on layer-by-layer assembly of multilayer flims composed of chitosan, gold nanoparticles and glucose oxidase modified Pt electrode", Biosensor and Bioelectronics, vol. 22, Jan. 2007, p. 838-844.*
Guiseppi-Elie, et al., "Direct Electron Transfer of Glucose Oxidase on Carbon Nanotubes", Nanotechnology (2002), vol. 13, pp. 559-564.

* cited by examiner

*Primary Examiner* — J. Christopher Ball
(74) *Attorney, Agent, or Firm* — Posternak Blankstein & Lund LLP

(57) ABSTRACT

A glucose sensor suitable for measuring glucose levels in human saliva is provided. Systems containing the glucose sensor and methods for making and using the sensor are also provided. The glucose sensor is highly sensitive and can detect glucose levels at least down to 5 ppm. Fabrication of the sensor involves depositing single-walled carbon nanotubes onto the surface of a working electrode in a 3 electrode electrochemical detector and functionalizing the nanotubes by depositing layers of polymers, metallic nanoparticles, and glucose oxidase enzyme onto the nanotubes. The sensor can be used as a disposable, single-use device or as part of an analytical system, such as a microfluidics system, for the analysis of multiple analytes. The sensor enables the diagnosis and monitoring of diabetes to be performed without pain or the need for finger pricks in a home or clinical setting.

18 Claims, 18 Drawing Sheets

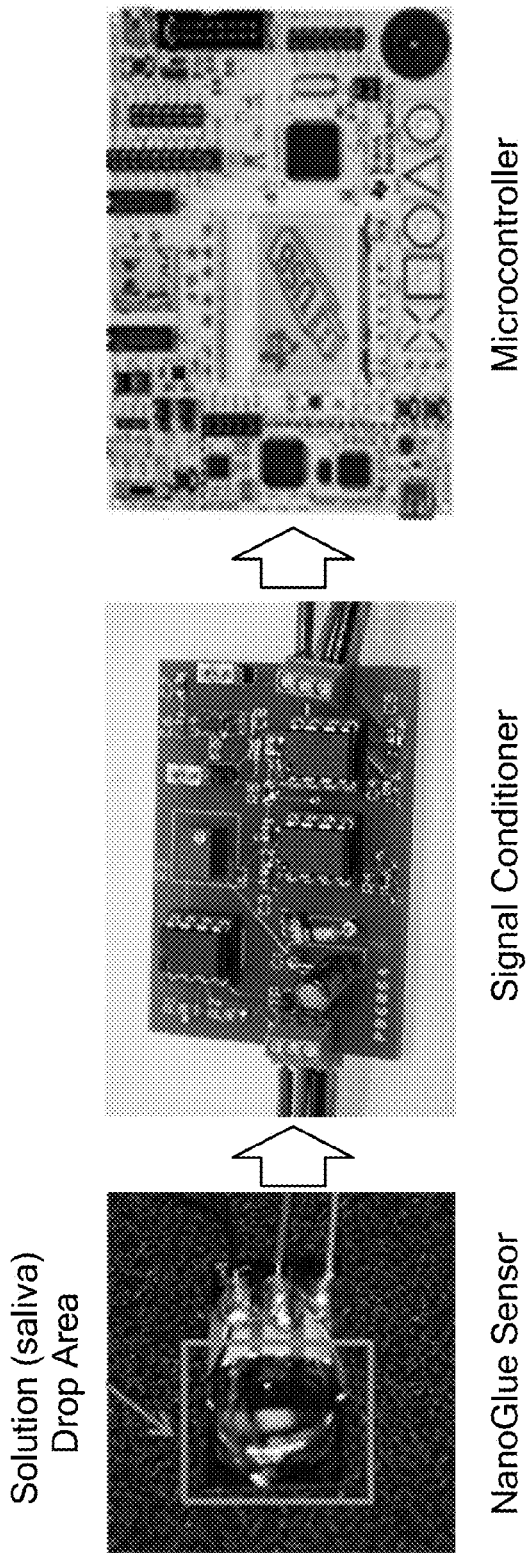

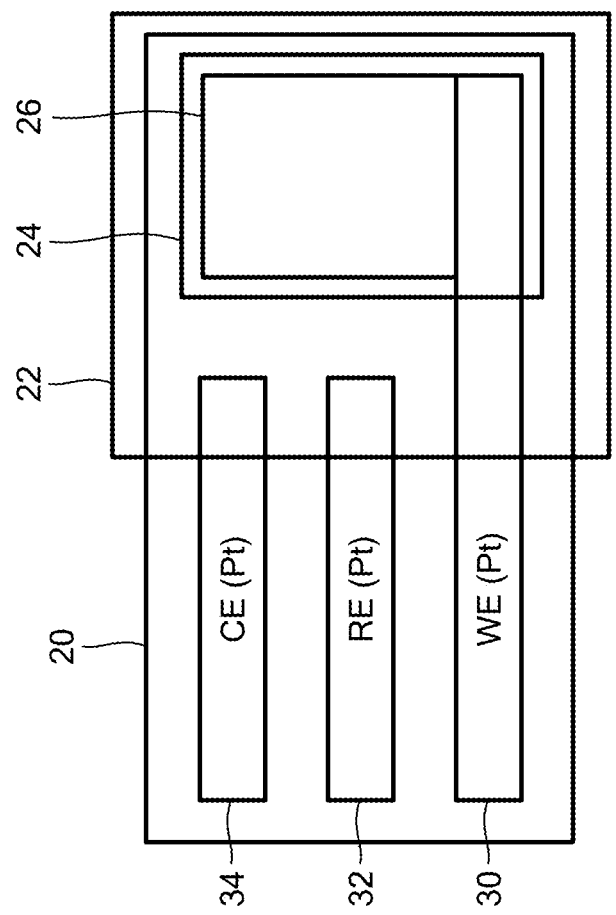
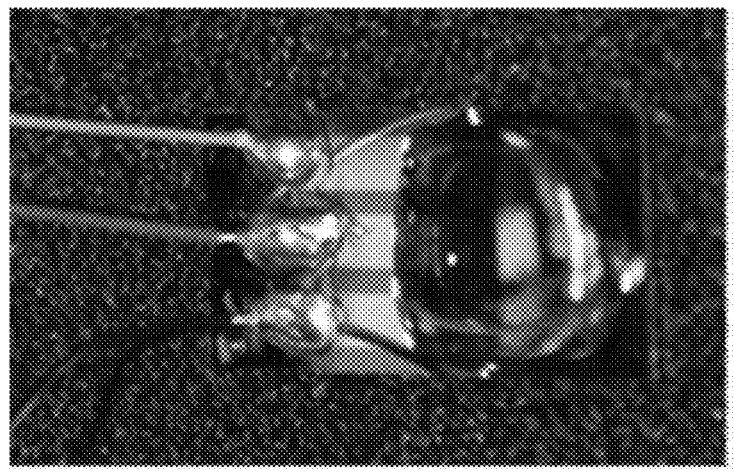
*FIG. 2A*
*FIG. 2B*

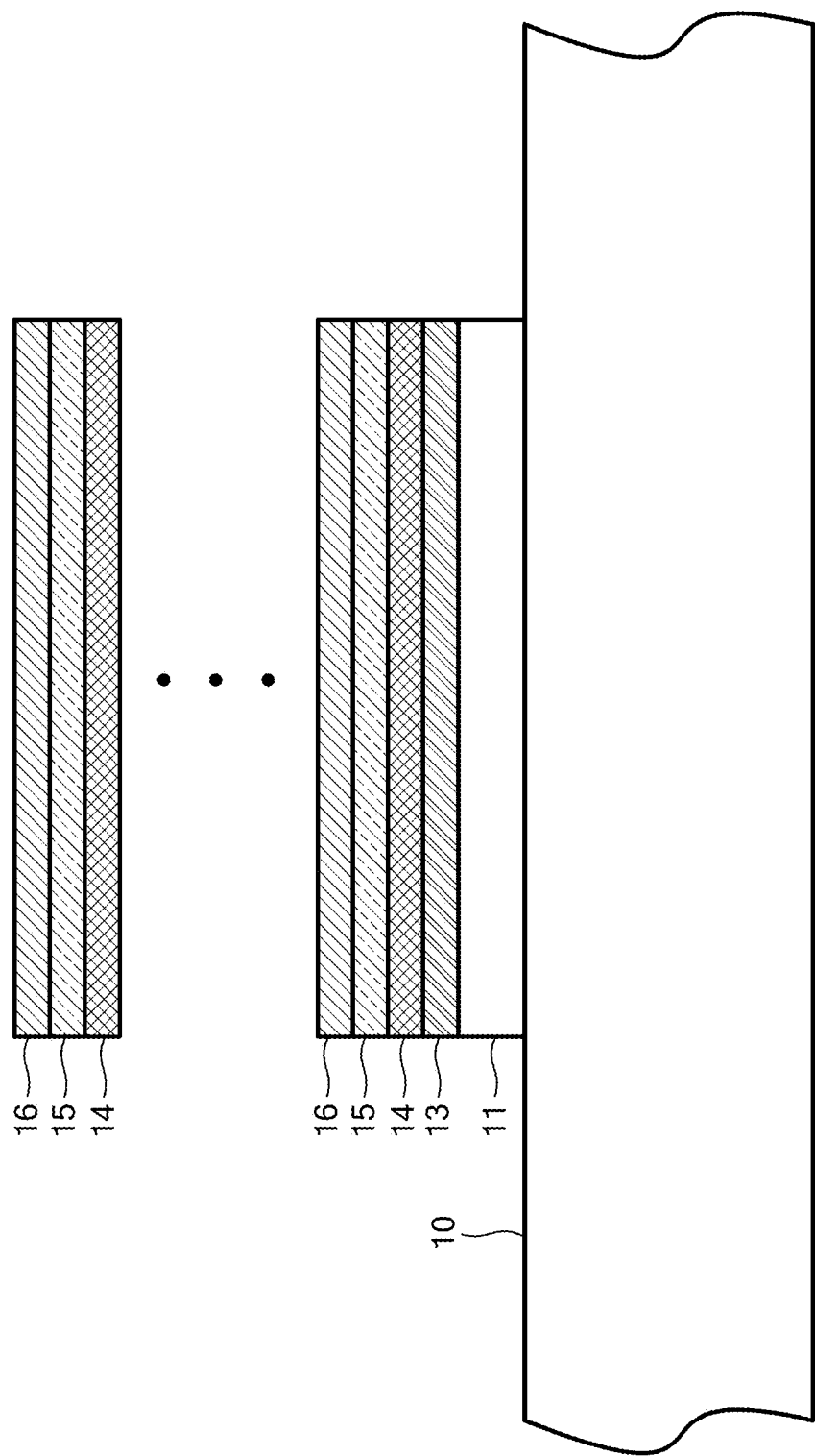

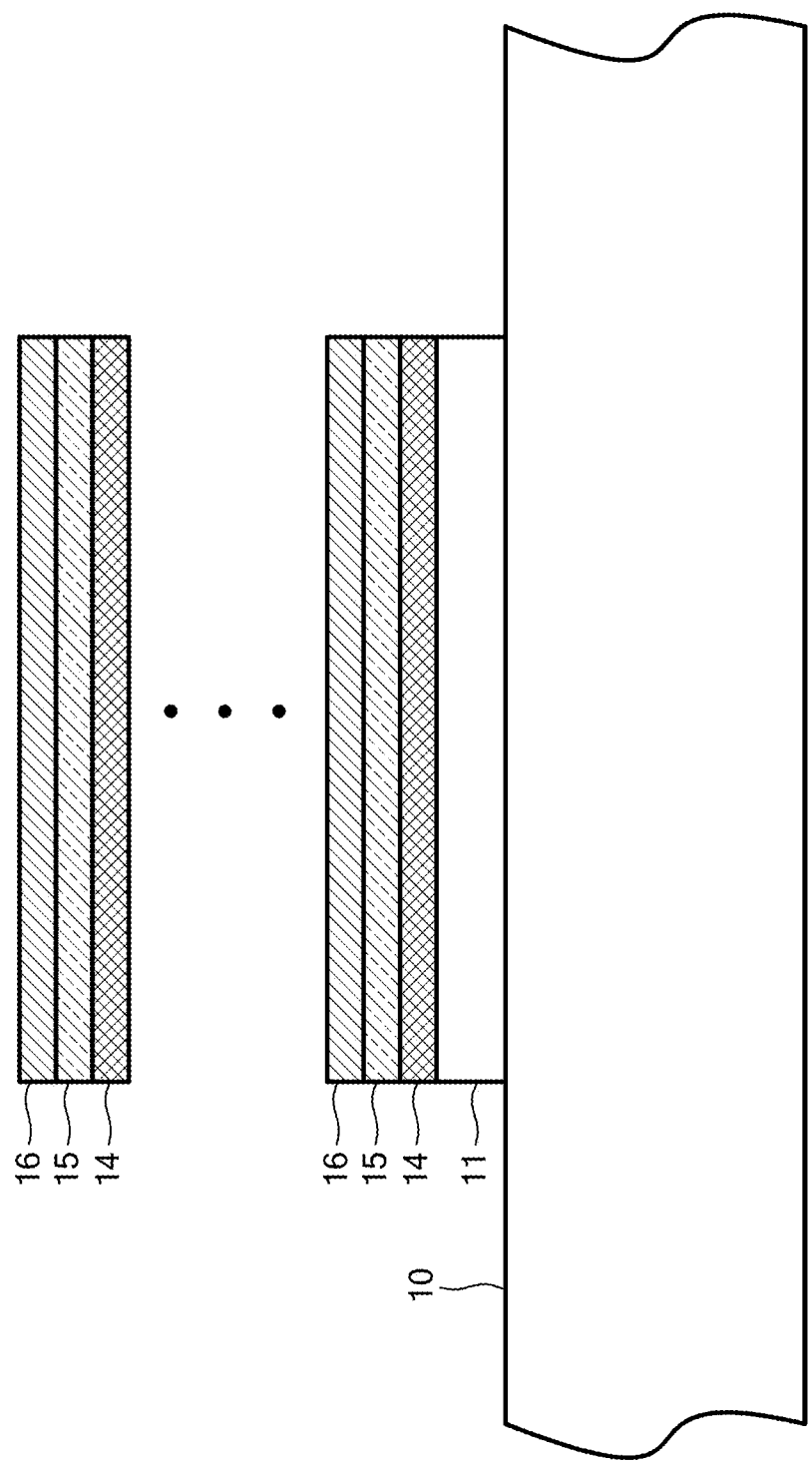

SALIVA GLUCOSE MONITORING SYSTEM

CROSS REFERENCE TO RELATED APPLICATIONS

This application claims the priority of U.S. Provisional Application No. 61/751,451 filed 11 Jan. 2013 and entitled "Saliva Glucose Monitoring System"; and U.S. Provisional Application No. 61/860,519 filed 31 Jul. 2013 and entitled "Saliva Glucose Monitoring System". Both of said provisional applications are hereby incorporated by reference in their entireties.

BACKGROUND

A statistical analysis by the World Health Organization (WHO) indicates that more than 220 million people have to live with diabetes (1). Diabetes caused over 1.1 million deaths in 2005, and 4 million in 2011. Estimates show that 4.8 million people died in 2012 from complications of the disease, with people under 60 accounting for half the deaths (www.cbsnews.com/8301-204_162-57549731/371-million-people-have-diabetes-globally-about-half-undiagnosed/). Early diagnosis, on time treatment, and continuous management are vital to ensure patients' quality of life and to avoid circulatory problems and diseases caused by diabetes, such as kidney failure, heart disease and blindness (1-2). Current practice for diabetes management relies on monitoring blood glucose. There is a general dislike of the pain and inconvenience caused by finger pricking, leading to fewer tests and inadequate blood glucose control, which in turn results in more complications from the disease and significantly increased case management costs. Repeated painful finger sticks are a major problem for young children, and has similar negative consequences on disease management. Furthermore, finger pricking also can cause fainting and blood-borne infection (3-5).

Glucose sensing dates back to 1841 with glucose detection in urine, but the correlation between urine and plasma glucose has been shown to be inconsistent (6). There are currently many different glucose meters on the market for measuring blood glucose. However, to use these devices, patients have to prick their finger for a drop of blood multiple times a day. Other techniques have been developed which employ minimally invasive or noninvasive techniques for blood glucose monitoring, including infrared (IR) spectroscopy (7-9), fluorescence spectroscopy (10-11), Raman spectroscopy (12-13), optical polarization rotation measurement (14-17), photoacoustic probes (18), and surface plasmon resonance (19-20). Results from these techniques are limited by spectral signal-to-noise levels and sample thickness, and have to be correlated with direct blood glucose measurements. While methods based on optical measurements are available (see, e.g., the OrSense NBM device described at www.orsense.com/files/files/Journal of Diabetes Science and Technology.pdf), most are for laboratory use only and are not suitable for routine glucose monitoring at home due to the size, cost, and complexity of operation of the required equipment. One instrument based on the detection of glucose in human sweat has been marketed for diabetes diagnosis. However, the difficulty of use due to the sweat collection process and the level of accuracy have resulted in its removal from the market. Another product detects blood glucose concentration via an optical method called "occlusion spectroscopy" (21). However, for reasons of cost and simplicity of operation there remains a need for a convenient, easy to use, and low cost glucose sensor.

Many studies have demonstrated that there is a correlation between blood glucose and saliva glucose levels (22-26). The application of saliva glucose measurements directly to indicate the health conditions of an individual is theoretically possible and appears realistic. It is reported that salivary glucose levels are significantly higher in diabetic patients than in people without diabetes under similar conditions (27-29). Thus, measurement of saliva glucose level can be utilized as an alternative diagnostic method for diabetics and as a health indicator of a subject who is normal or suspected of having diabetes. There are reported measurements of glucose in saliva using optical measuring systems such as a liquid chromatography-mass spectrometer (LC-MS) or a UV-visible spectrophotometer (22, 24-26). However, the cost of the instruments is very high and their operation is complicated and time consuming, making them unsuitable for everyday personal use. Therefore, these methods cannot be used for individual glucose monitoring at home or in the course of daily activities. Until now, there has not been a suitable technology for home measurement of glucose using saliva because there wasn't an easy to use, low-cost sensor system sensitive enough to detect the low levels of glucose present in saliva.

SUMMARY OF THE INVENTION

The present invention provides a highly sensitive glucose sensor adapted for detection of glucose in saliva samples using an electrochemical method. The saliva glucose sensor is suitable for use in diagnosing diabetes and monitoring glucose levels in diabetic patients or any mammalian subjects using only a small amount of unmodified saliva, and with results obtained in seconds. The sensor is provided in both reusable and single use embodiments, and can also be integrated into a fluidic system for processing of the sample, measurement of glucose and/or other analytes, and the results can be analyzed within the device and/or transmitted to remote analysis, monitoring, or data storage facility.

One aspect of the invention is a glucose sensor for determining a concentration of glucose in a liquid sample. The sensor includes an insulating or semiconducting substrate, at least one working electrode, a counter electrode, and a reference electrode, as well as a sample placement area on the surface of the substrate for containing the liquid sample during a determination of the glucose concentration in the liquid sample. Each of the working electrode(s), counter electrode, and reference electrode includes a conductive metal layer deposited on the substrate in the sample placement area. The working electrode is optionally coated in the sample placement area with a plurality of sensor elements. The sensor elements (or the working electrode in the sample placement area, if no sensor elements are present) are functionalized with a coating containing glucose oxidase. The working electrode, counter electrode, and reference electrode are each connected to an amperometry circuit, whose output voltage provides a measure of the glucose concentration in the liquid sample deposited in the sample placement area. The output signal of the detection circuit is correlated to the glucose concentration in the liquid sample by a function. For example the output signal can be proportional to the glucose concentration, or related by some other function which can be determined using a set of liquid samples having calibrated glucose concentrations. Preferably, the sensor, or batch of sensors, is calibrated by determining a calibration curve using a range of different glucose concentrations.

In embodiments of the glucose sensor, the substrate includes a material selected from the group consisting of silicon, glass, ceramic, a non-conductive polymer, and combinations thereof.

In embodiments of the glucose sensor, the working electrode includes one or more materials selected from the group consisting of gold, platinum, iridium, silver, silver/silver chloride, and combinations thereof.

In embodiments of the glucose sensor, the sensor elements (if present) include or consist of a material selected from the group consisting of single-walled carbon nanotubes (SWNT), graphite, graphene, carbon nanofibers, carbon nanowires, and combinations thereof.

In embodiments of the glucose sensor, the sensor element functionalization coating includes one or more layers, and each layer includes a sublayer of chitosan, a sublayer of gold nanoparticles disposed on the sublayer of chitosan, and a sublayer of glucose oxidase disposed on the sublayer of gold nanoparticles.

In embodiments of the glucose sensor, the sensor further includes a layer containing a polycationic polymer; this layer is deposited on the surface of the working electrode and beneath the sensor elements. In different embodiments, the polycationic polymer is selected from the group consisting of polyallylamine, poly(L-lysine), polyethyleneimine, polyamidoamine dendrimers, and combinations thereof.

In embodiments of the glucose sensor, the sensor element functionalization coating comprises one or more materials selected from the group consisting of carbon nanotubes, graphite, gold nanoparticles, platinum nanoparticles, serum albumin, chitosan, and Prussian Blue.

In certain embodiments of the glucose sensor, the sensor includes a sensor element protective membrane which covers the electrodes to protect the functionalization coating and limit exposure of the coating to contamination from the liquid sample. The membrane may include or consist of Nafion or a lipid bilayer membrane, or another type of semi-permeable membrane.

In certain embodiments, the glucose sensor is a component of a microfluidics device, which device includes one or more channels that deliver a liquid sample to the sample placement area of the sensor.

In embodiments of the glucose sensor, the sensor is capable of detecting glucose at concentrations down to 5 ppm (0.5 mg/dL) or lower. Embodiments of the sensor can be configured for determination of glucose concentration in saliva, and also can be configured as either a disposable device or as a reusable device. Certain embodiments of the glucose sensor contain one or more working electrodes having functionalized sensor elements capable of detecting an analyte that is not glucose; such embodiments can be used for multiplex analysis of one or more other analytes which are not glucose.

Another aspect of the invention is a glucose analysis system. The system includes the above-described glucose sensor and a signal conditioning and/or analysis device that processes an electrical signal from the sensor. The analysis system may also include a transmitter device for sending a radio signal to a remote receiver and/or to a data processing device. The radio signal carries information related to a glucose concentration in the liquid sample; the information is obtained from the signal conditioning and/or analysis device. The analysis system may also include a memory device for accumulating data related to the glucose concentration in the liquid sample; the data can be obtained at different times or from different liquid samples. The analysis system may also include a device for chemically or physically processing a liquid sample and delivering the processed sample to the sample placement area of the device.

Yet another aspect of the invention is a method of determining a glucose concentration in a liquid sample. The method includes the steps of: (a) providing the glucose sensor described above, or the glucose analysis system described above; (b) introducing a liquid sample into the sample placement area of the sensor; and (c) determining the glucose concentration in the liquid sample from an electrical output of the sensor. In certain embodiments of the method, the following additional steps are performed: (d) removing the liquid sample introduced in step (b); (e) introducing a new liquid sample into the sample placement area of the sensor; and (f) determining a new glucose concentration in the new liquid sample from an electrical output of the sensor. In embodiments of the method, the liquid sample is from a subject who has diabetes or is suspected of having diabetes. In certain embodiments of the method, the liquid sample is from a subject who is tested as part of a health screening process. In embodiments of the method, the liquid sample is a saliva sample, such as a human saliva sample.

Still another aspect of the invention is a method of fabricating a glucose sensor. The method includes the steps of: (a) fabricating a working electrode, a reference electrode, and a counter electrode on the surface of an insulating substrate, wherein each of said electrodes contacts a sample placement area on the substrate; (b) optionally depositing a layer of a polycationic polymer onto the working electrode; (c) optionally depositing a plurality of sensor elements onto the polycationic polymer layer or onto the working electrode; and (d) depositing a plurality of functionalization layers onto the sensor elements or onto the working electrode, the functionalization layers including sublayers of chitosan, gold nanoparticles, and glucose oxidase. In certain embodiments, the method further includes the step of: (e) depositing a sensor element protective membrane over the functionalization layers of the sensor elements. The protective membrane can include or consist of Nafion or a lipid bilayer.

In embodiments of the method, the substrate includes a material selected from the group consisting of silicon, glass, ceramic, a non-conductive polymer, and combinations thereof. In embodiments of the method, the working electrode contains one or more materials selected from the group consisting of gold, platinum, iridium, silver, silver/silver chloride, and combinations thereof. In embodiments of the method, the sensor elements comprise a material selected from the group consisting of single-walled carbon nanotubes (SWNT), graphite, graphene, carbon nanofibers, carbon nanowires, and combinations thereof. In embodiments of the method, the polycationic polymer (if present) is selected from the group consisting of polyallylamine, poly(L-lysine), polyethyleneimine, polyamidoamine dendrimers, and combinations thereof. In embodiments of the method, one or more of the functionalization layers contain a material selected from the group consisting of carbon nanotubes, graphite, gold nanoparticles, platinum nanoparticles, serum albumin, chitosan, and Prussian Blue. In embodiments of the method, the sensor elements are deposited on the working electrode by a self-assembly process comprising depositing a liquid suspension of sensor elements onto the layer of polycationic polymer. In embodiments of the method, the method includes depositing two or more working electrodes onto the substrate, each having differently functionalized sensor elements. In certain embodiments, the differently functionalized sensor elements can detect different analytes. In embodiments of the method, one or more of the electrodes is deposited such that it is not coplanar with the other electrodes. Each electrode can be deposited at a different layer or different level than the others with respect to the substrate surface, i.e., at, below, or above the plane of the substrate surface.

Another aspect of the invention is a glucose sensor array including a plurality of the above-described glucose sensors sharing a common substrate.

Yet another aspect of the invention is a glucose sensing functionalization coating. The coating can be applied to an electrode of an electrochemical cell to render the electrode selective for detecting glucose in a solution. The coating includes one or more layers, each layer containing a sublayer of chitosan, a sublayer of gold nanoparticles disposed on the sublayer of chitosan, and a sublayer of glucose oxidase disposed on the sublayer of chitosan. In embodiments, the glucose sensing functionalization coating further includes one or more materials selected from the group consisting of carbon nanotubes, graphite, gold nanoparticles, platinum nanoparticles, serum albumin, chitosan, and Prussian Blue. In embodiments of the glucose sensing functionalization coating, a lowermost layer of the coating further includes a sublayer of sensing elements beneath the sublayer of chitosan. In embodiments, the sensor elements include or consist of a material selected from the group consisting of single-walled carbon nanotubes (SWNT), graphite, graphene, carbon nanofibers, carbon nanowires, and combinations thereof. In embodiments, the coating further includes a layer of a cationic polymer beneath the sensing elements. The polycationic polymer can be selected from the group consisting of polyallylamine, poly(L-lysine), polyethyleneimine, polyamidoamine dendrimers, and combinations thereof.

Still another aspect of the invention is a glucose-sensing electrode containing a metallic or conductive material coated with the above-described glucose sensing functionalization coating.

BRIEF DESCRIPTION OF THE DRAWINGS

FIG. 1A shows a photograph of the sample application area of an embodiment of a saliva glucose sensor according to the invention. The rectangle indicates the sample area where a drop of saliva is deposited. The sample area includes three electrodes on the lower surface, each of which contacts the drop of saliva, and each connected to a lead providing signal to the signal conditioning electronic module shown in FIG. 1B. The conditioned signal is then passed to the microcontroller module shown in FIG. 1C, which can perform calculations, analyze the data, and store the data or transmit it to an external receiver (not shown).

FIG. 2A is a schematic representation of an embodiment of the electrode portion 20 of a saliva glucose sensor of the invention. Working electrode 30, reference electrode 32, and counter electrode 34 are arranged in parallel, each extending into sample area 22 where saliva is deposited and contacts each of the three electrodes. The working electrode extends into the sample area where it forms sample contact pad 26. A portion 24 of the working electrode, including the sample contact pad, is coated with a glucose detection coating according to the invention. FIG. 2B shows a photograph of an actual sensor constructed according to the layout shown in FIG. 2A.

FIGS. 3C-1 and 3C-2 show a schematic representation of an embodiment of a process for functionalizing SWNT for glucose detection. Functionalization is accomplished by applying a coating using the bonding mechanism shown, in which the substrate has a positively charged surface to which SWNT are bonded. FIG. 3D shows a cross-section of the saliva glucose sensor as fabricated according to FIGS. 3C-1 and 3C-2. The layers of the sensor are indicated as follows: 10—insulating or semiconducting substrate (e.g., silicon or ceramic material); 11—conductive metal layer (e.g., platinum); 13—SWNT layer; 14—chitosan layer (CS); 15—gold nanoparticle layer (GNp); and 16—glucose oxidase layer (GOx).

FIGS. 3E-1 and 3E-2 show a schematic representation of an embodiment of a process for functionalizing SWNT for glucose detection. Functionalization is accomplished by applying a coating using the bonding mechanism shown, in which the surface of the substrate has a rough texture to which SWNT are bonded.

FIG. 3H shows a cross-section of the saliva glucose sensor as fabricated according to FIG. 3G. The layers of the sensor are indicated as follows: 10—insulating or semiconducting substrate (e.g., silicon or ceramic material); 11—conductive metal layer (e.g., platinum); 14—chitosan layer (CS); 15—gold nanoparticle layer (GNp); and 16—glucose oxidase layer (GOx).

DETAILED DESCRIPTION OF THE INVENTION

Figures 1, 3A:
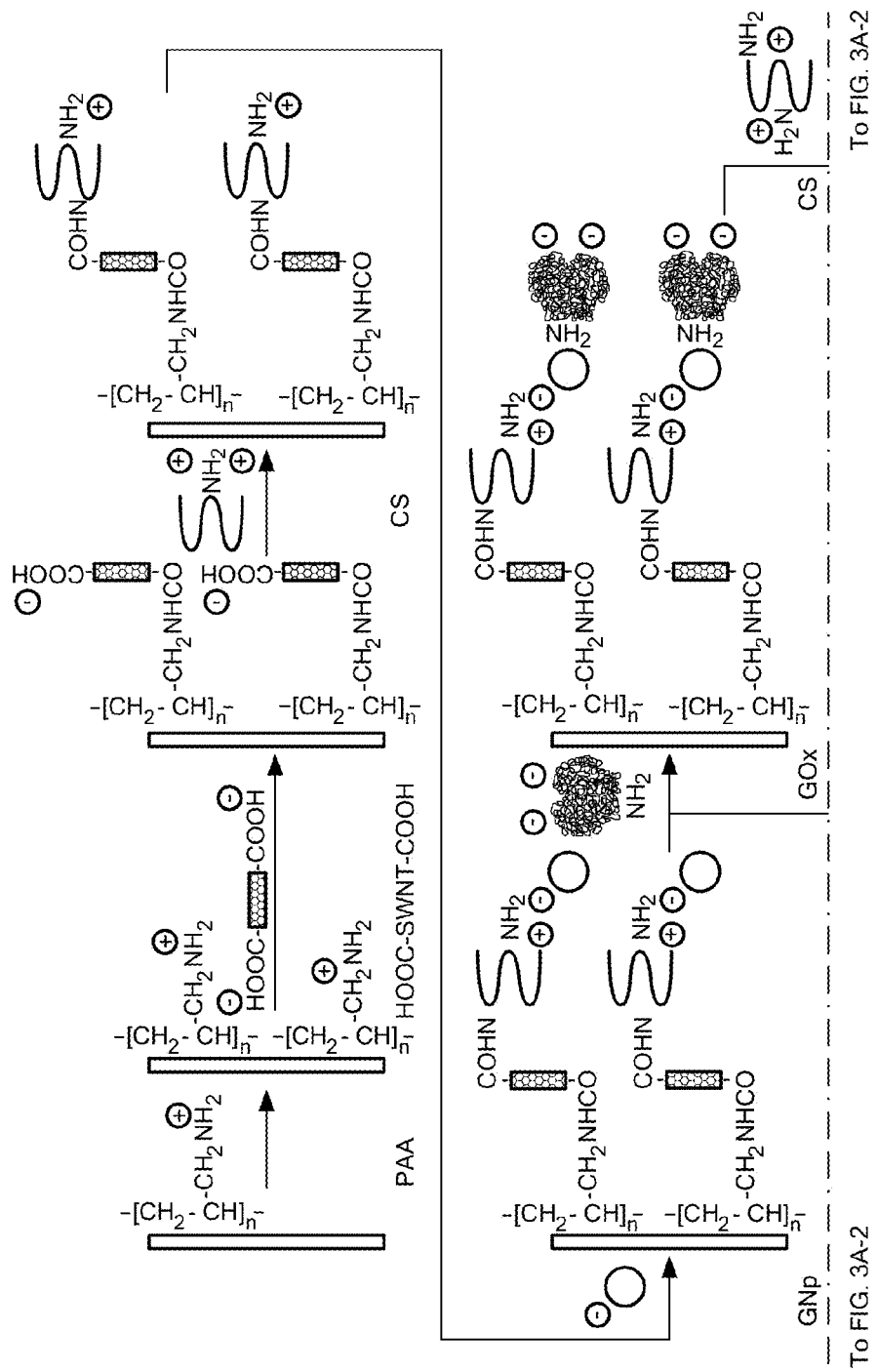
FIGS. 3A-1 and 3A-2 show a schematic representation of an embodiment of a process for functionalizing SWNT for glucose detection. Functionalization is accomplished by applying a coating using the bonding mechanism shown.

The present invention provides a painless test methodology using a highly sensitive glucose sensor and associated electrochemical system adapted for detection of glucose in saliva samples. The saliva glucose sensor of the invention is suitable for use in screening for and diagnosing diabetes, as well as to monitor glucose control by individual diabetic patients or test subjects, in any setting (including at home or in a clinic) and using only a small amount of unmodified human saliva, with results obtained in seconds.

The present invention measures saliva glucose level in real time through the use of the glucose sensor described herein. An object of the invention is to measure small amounts of glucose in saliva. The invention can replace current blood glucose monitors in many applications because it is noninvasive and can be used easily and without pain, apprehension, or anxiety. It is sensitive to physiological changes of saliva glucose which parallel changes in blood glucose, and therefore is effective and useful for real time tracking of glucose levels using saliva at any time, including at regular intervals or times prescribed by a physician, while at home, at work, or on travel.

The saliva glucose sensor of the present invention can be used as part of a real-time noninvasive saliva glucose monitoring system. The system contains a saliva sampling mechanism, an enzyme-based electrode biosensor, a glucose meter, signal processing components, and a display for outputting the results. The saliva sampling mechanism optionally can include a collector for collecting saliva from the oral cavity as well as saliva filtration and/or saliva pretreatment modules, which may enhance reliability of sampling and accuracy of results. The biosensor is an electrochemical system which can include a three- or four-electrode cell on a single chip. Multiple identical or non-identical sensors can be included on a single chip or substrate, so that assays can be carried out with enhanced reliability and/or in multiplex format.

One embodiment includes single-walled carbon nanotubes (SWNT) applied as a coating to the working electrode. The SWNT can be, for example, a mixture of metallic and semiconducting SWNT. The SWNT provide an extremely large surface-to-volume ratio and have useful electrical properties. A sensor according to the present invention operates by an electrochemical mechanism, whereby the presence of a particular analyte causes electron transfer in the electrochemical system, which can be identified and quantified by measuring a current through the sensor, which can be converted via amperometry to an output voltage. This feature of the present sensor renders it more accurate and reliable than other types of sensors that produce a change in electrical resistance of SWNT in the presence of an analyte.

The electrode material can contain or consist of, for example and without limitation, gold, platinum, iridium, silver, silver/silver chloride, copper, aluminum, chromium, or other conductive metals or other conductive materials, or any combination thereof. In one embodiment, the SWNT are functionalized by a coating that includes an enzyme that catalyzes an electron transfer reaction and is specific for the selected analyte, such as glucose. Preferably the reaction is an oxidation reaction. For example, for the detection of glucose as the analyte, the enzyme glucose oxidase (GOx, EC 1.1.3.4) can be used, which specifically catalyzes the oxidation of β-D-glucose to hydrogen peroxide and D-glucono-δ-lactone, which then hydrolyzes to gluconic acid. The enzyme can be a naturally occurring glucose oxidase enzyme which is isolated from a natural source (e.g. cells of *Aspergillus niger*), or it can be produced recombinantly in transformed or transfected host cells, such as bacterial cells, yeast or fungal cells, or mammalian cells. It can be glycosylated or non-glycosylated. The glucose oxidase enzyme used in the sensor can have a naturally occurring amino acid sequence, or it can have a mutant or engineered amino acid sequence. Different enzyme-functionalized SWNT can be combined in a multiplex sensor that takes advantage of the different sensitivities of each enzyme and their different resistance to inhibition induced by potentially interfering substances that might be encountered in a saliva sample.

The sensor detects levels of glucose in saliva or another fluid by keeping track of the electrons passed through the glucose oxidase enzyme coated on the working electrode and measuring the resulting current, which is detected by an amperometry detection circuit and expressed as a change in output voltage. The sensing performance can be further improved by modifying the enzyme-coated electrode with various materials, including biomolecular or porous films or membranes. Such materials include, but are not limited to, carbon nanotubes, graphite, nanowires, gold nanoparticles (GNp), Pt nanoparticles, chitosan, bovine serum albumin (BSA), and Prussian Blue or other materials with similar properties. In one embodiment, the sensor of the present invention detects glucose via an electrical signal resulting from the glucose oxidase reaction performed on functionalized SWNT connected to a detection circuit. It does not require any additional chemical reactions (e.g. peroxidase reaction) or optical detection means to detect the reaction products.

One embodiment of the sensor is shown in FIG. 1. The signal conditioner and microcontroller can be substituted by any existing device for electrochemical analysis, and can be configured for stationary use (i.e., as a fully contained or standalone unit) or for remote use (i.e., containing a transmitter for wireless communication with a separate data analysis system), as well as for continuous monitoring using a microfluidic system. The core of the system is the sensor containing SWNT that have been functionalized with glucose oxidase enzyme.

Figures 2, 3A:
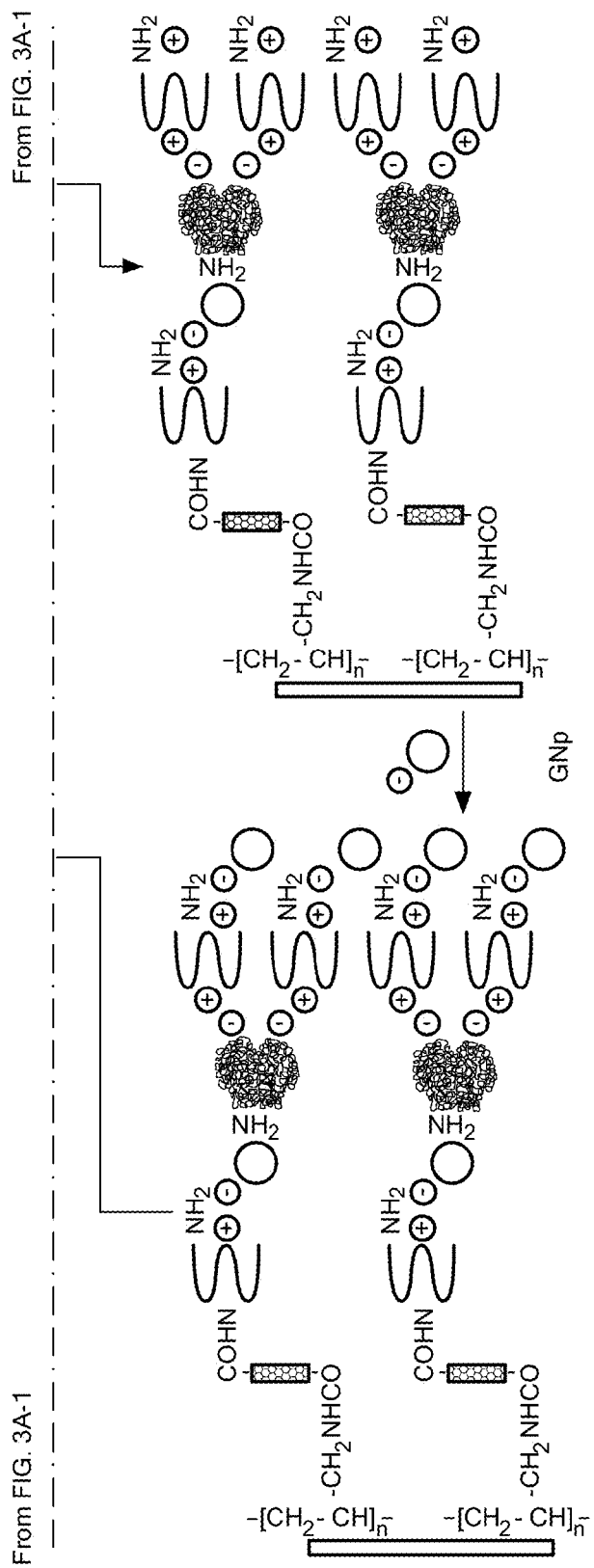

The sensor typically contains three electrodes: a working electrode, a counter electrode, and a reference electrode. Glucose oxidase is attached to a component of the working electrode. Solution containing glucose is dropped onto the sensor where it touches all three electrodes. The amount of glucose present is measured via an amperometric method. The geometry of the electrodes and proportion of areas among them preferably is optimized to yield the best results for the volume of saliva used for the test. An example is shown in FIG. 2. The saliva volume can be in the range from a few nanoliters to several milliliters or more.

In order to functionalize the nanosensor for glucose detection in saliva, the working electrode can be coated with a multilayered structure containing glucose oxidase (GOx). The procedure of coating GOx onto the working electrode involves a layer-by-layer assembly to form a multilayer film. In one embodiment, each layer contains sublayers of chitosan, gold nanoparticles, and glucose oxidase. Such coating materials provide the best results in terms of accuracy, repeatability, and durability. Polyallylamine (PAA) or another cationic polymer can be used to modify the electrode surface prior to coating with SWNT. PAA provides amino groups, which are highly positively charged and can be adsorbed on the surface of a working electrode, such as a Pt electrode. SWNT can be deposited on the substrate surface, or more preferably on the surface of the PAA layer, by adding an aqueous suspension of SWNT and allowing the SWNT to adhere to the surface. The combination of functionalized SWNT and a layer-by-layer coating process greatly increases the detection accuracy and sensitivity, allowing the detection of low levels of glucose in saliva in clinically relevant ranges with a response time of down to 10-20 seconds or less. The sensor geometry and the number of layers can be optimized to improve accuracy and sensitivity. The sensing principal is the same, regardless of the sensor geometry and the number of coating layers used.

Figure 3B:
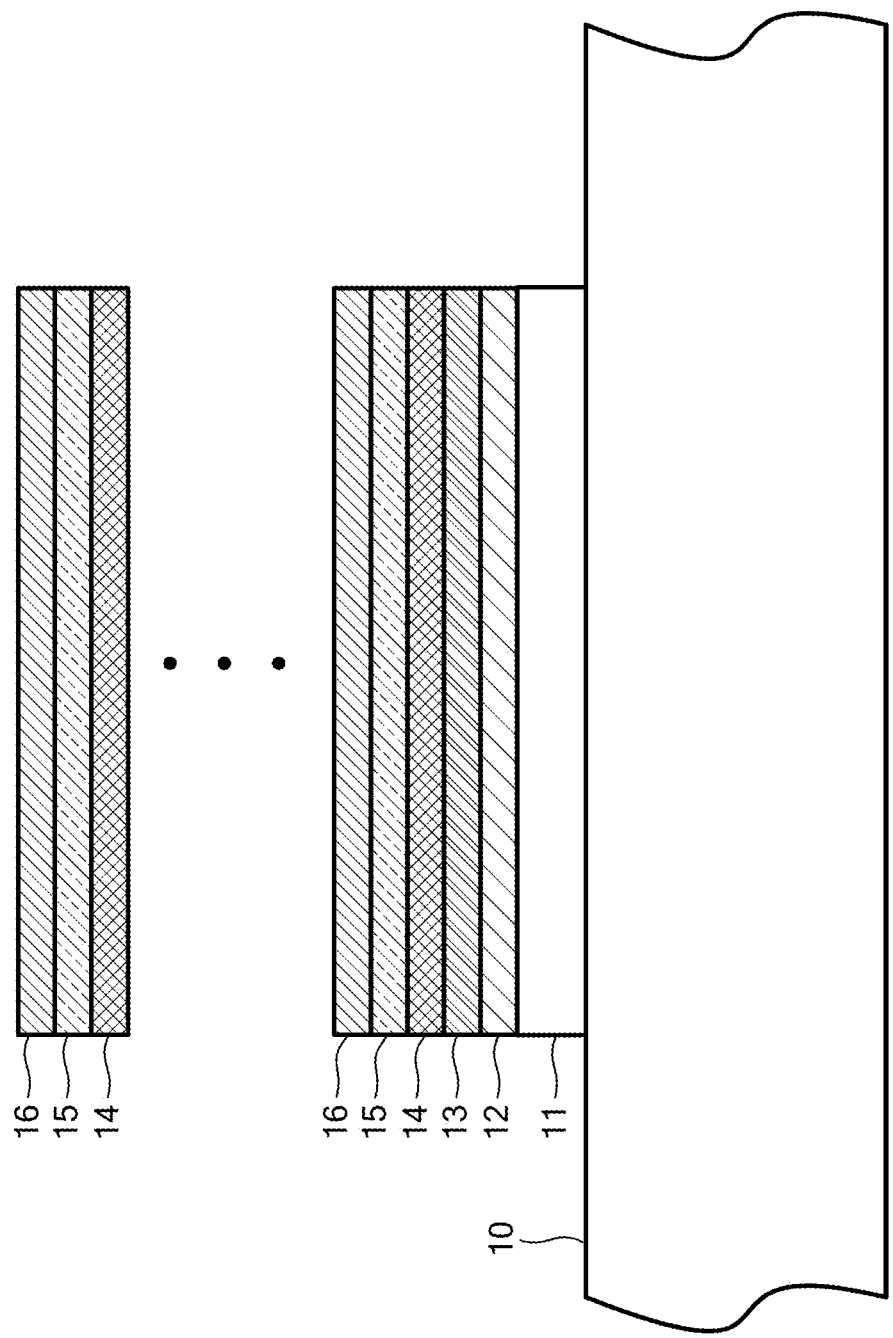
FIG. 3B shows a cross-section of the saliva glucose sensor as fabricated according to FIGS. 3A-1 and 3A-2. The layers of the sensor are indicated as follows: 10—insulating or semiconducting substrate (e.g., silicon or ceramic material); 11—conductive metal layer (e.g., platinum); 12—PAA layer; 13—SWNT layer; 14—chitosan layer (CS); 15—gold nanoparticle layer (GNp); and 16—glucose oxidase layer (GOx).

An example of a layer-by-layer assembly process of making a multilayer film to coat the working electrode is shown in FIGS. 3A and 3B. In this example each layer of the multilayer film is composed of sublayers of chitosan, gold nanoparticles, and glucose oxidase. One of the —COOH ends of the SWNT reacts with PAA on the electrode surface, forming a CO—NH bond, while the —COOH at the other end of the SWNT provides a negatively charged group that interacts with chitosan (CS) through an electrostatic attraction effect. Gold nanoparticles (GNp) are allowed to associate with CS and glucose oxidase through van der Waals forces. Such self-assembled combinations have been studied in other systems (42-43). The CS-GNp-GOx unit layer can be repeated several times to form a multilayered coating. The number of layers can be adjusted to achieve the best sensing performance. For example, the CS-GNp-GOx unit layer can repeated to form from 2 to 10 layers, or from 2 to 5 layers, or from 3 to 5 layers, or from 3 to 6 layers, or from 4 to 6 layers, or from 4 to 7 layers, or from 5 to 8 layers. A single layer of CS-GNp-GOx also can be used.

Other materials can be used to form the multilayer film and to coat the electrode surface. For example, PAA can be substituted with one or more other polycationic polymers, such as poly(L-lysine) (PLL), polyethyleneimine (PEI) and polyamidoamine dendrimers. SWNT can be substituted with graphite or carbon nanofibers and/or nanowires. GNp used anywhere in the invention can be substituted with nanoparticles of Pt, Ru, Sn, $Fe_3O_4$ or other metal or semiconductor nanoparticles. Chitosan can also be substituted with a layer of bovine serum albumin (BSA) or Prussian Blue, for example. The layer-by-layer assembly sequence can also be rearranged or altered using similar materials in a different arrangement or order as long as the type of bonds or van der Waals interactions as described above are satisfied. After the electrode is functionalized with glucose oxidase, a semi-permeable membrane, such as Nafion or a lipid bilayer membrane can be added to act as a filtration layer for filtering the liquid sample and also as a protection layer for glucose oxidase, so as to reduce its degradation. Preliminary results have indicated such added layers have no adverse effect that would slow the sensor response or reduce the sensitivity of detection of the low levels of glucose in saliva. The combination of appropriately functionalized SWNT and a layer-by-layer coating process greatly increases the accuracy of detection of the amount of glucose in saliva in clinically relevant ranges with a response time of 10-20 seconds or less. The capability of measuring such low concentrations of glucose and their correlation with blood glucose enables the sensor to not only detect hyperglycemia but also to detect hypoglycemia, which is very important in the monitoring and management of diabetes.

Figures 1, 3C:
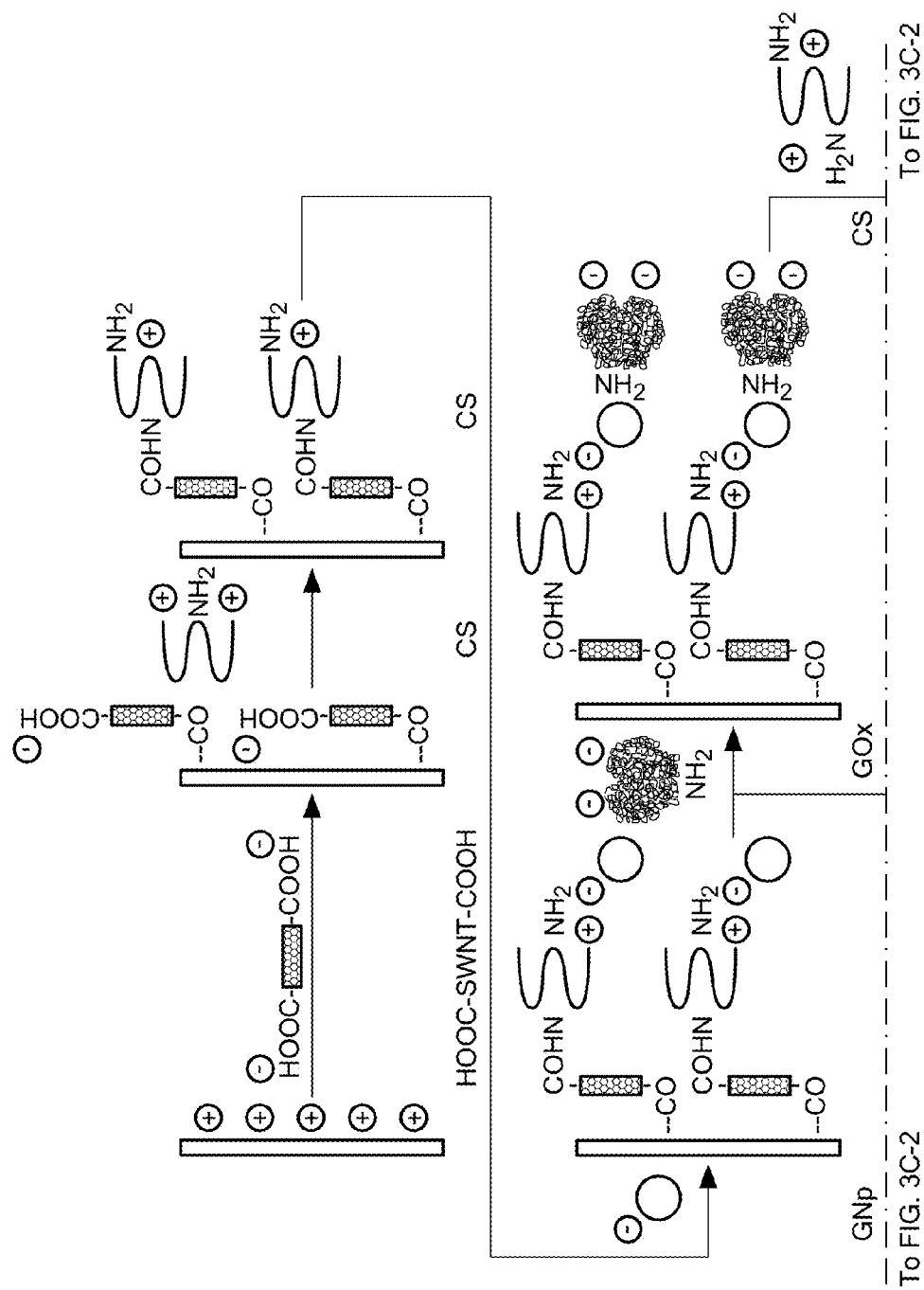
Figures 2, 3C:
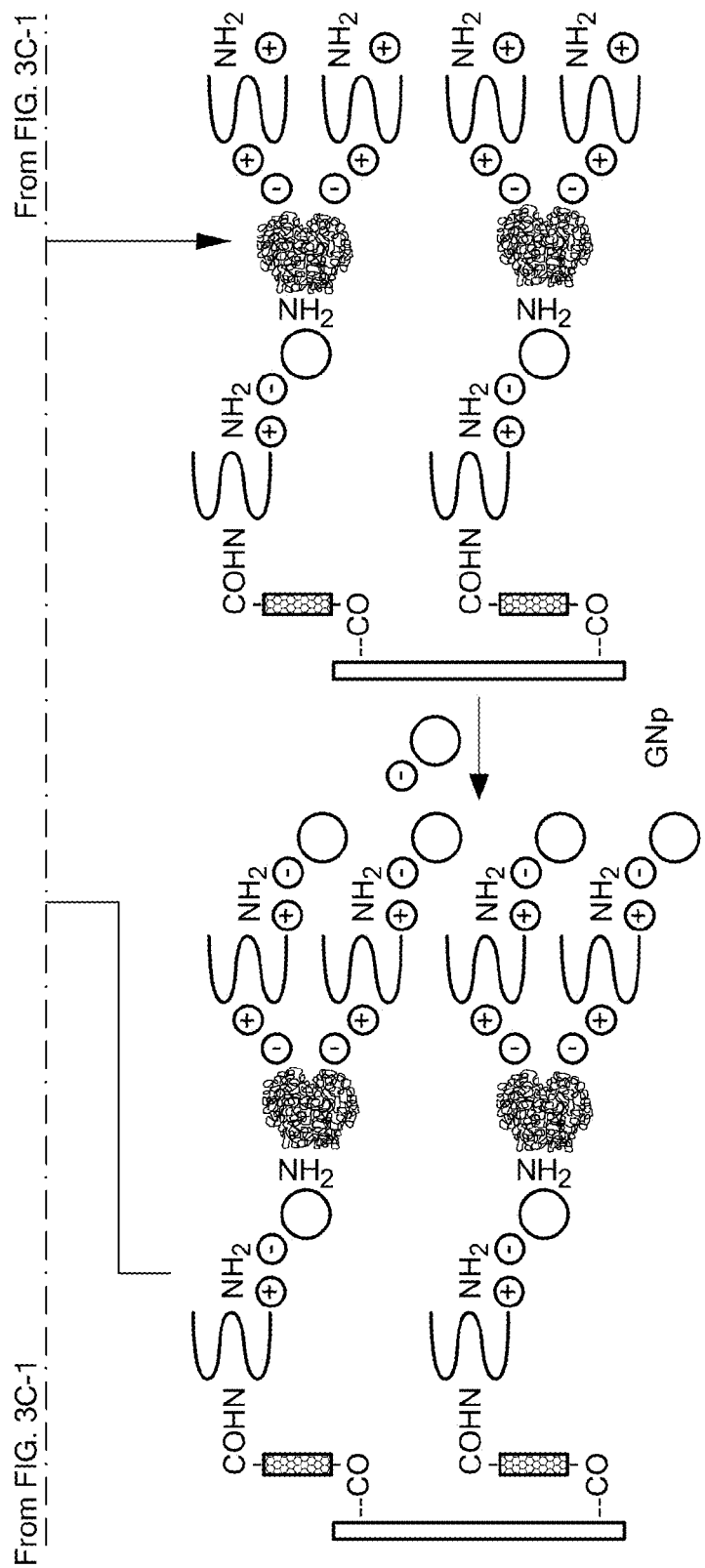

Another example of the assembly process of making a multilayer film to coat the working electrode is shown in FIGS. 3C and 3D. In this process, SWNT are directly deposited on the metal surface of the working electrode and attach to the surface of the electrode through non-covalent interactions. The electrode surface is not coated with PAA in this embodiment. In a variation of this method, the electrode surface is directly coated with chitosan, and is not coated with SWNT prior to the deposition of chitosan. In this process (regardless of whether SWNT are included or not), each layer of the multilayer film is again composed of sublayers of chitosan, gold nanoparticles, and glucose oxidase. Gold nanoparticles associate with chitosan and glucose oxidase (GOx) through non-covalent (e.g. van der Waals) forces. The CS-GNp-GOx unit layer may be repeated one or more times to form a multilayered coating. For high sensitivity, the CS-GNp-GOx unit layer is repeated to form several layers.

Figures 1, 3E:
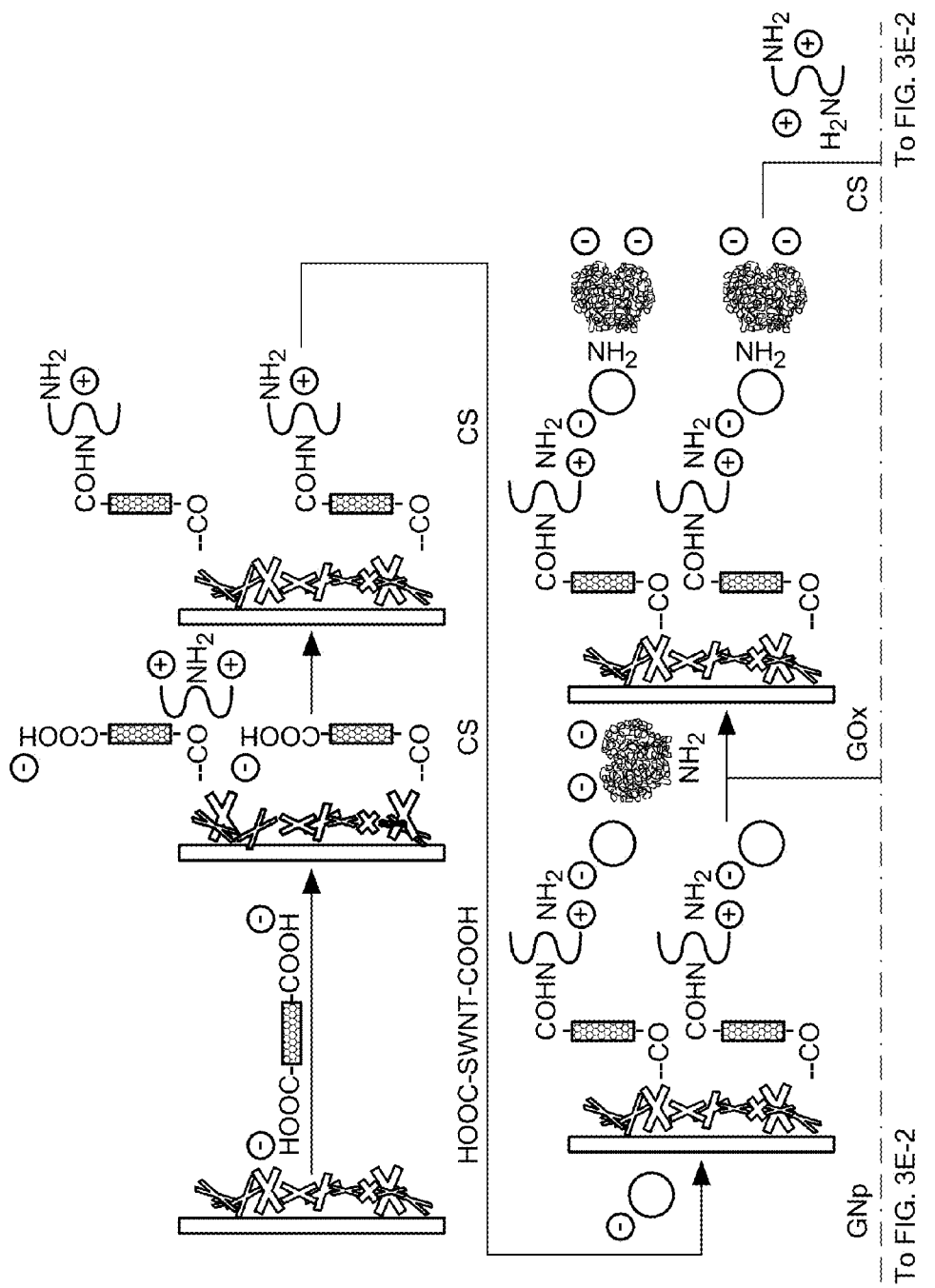
Figures 2, 3E:
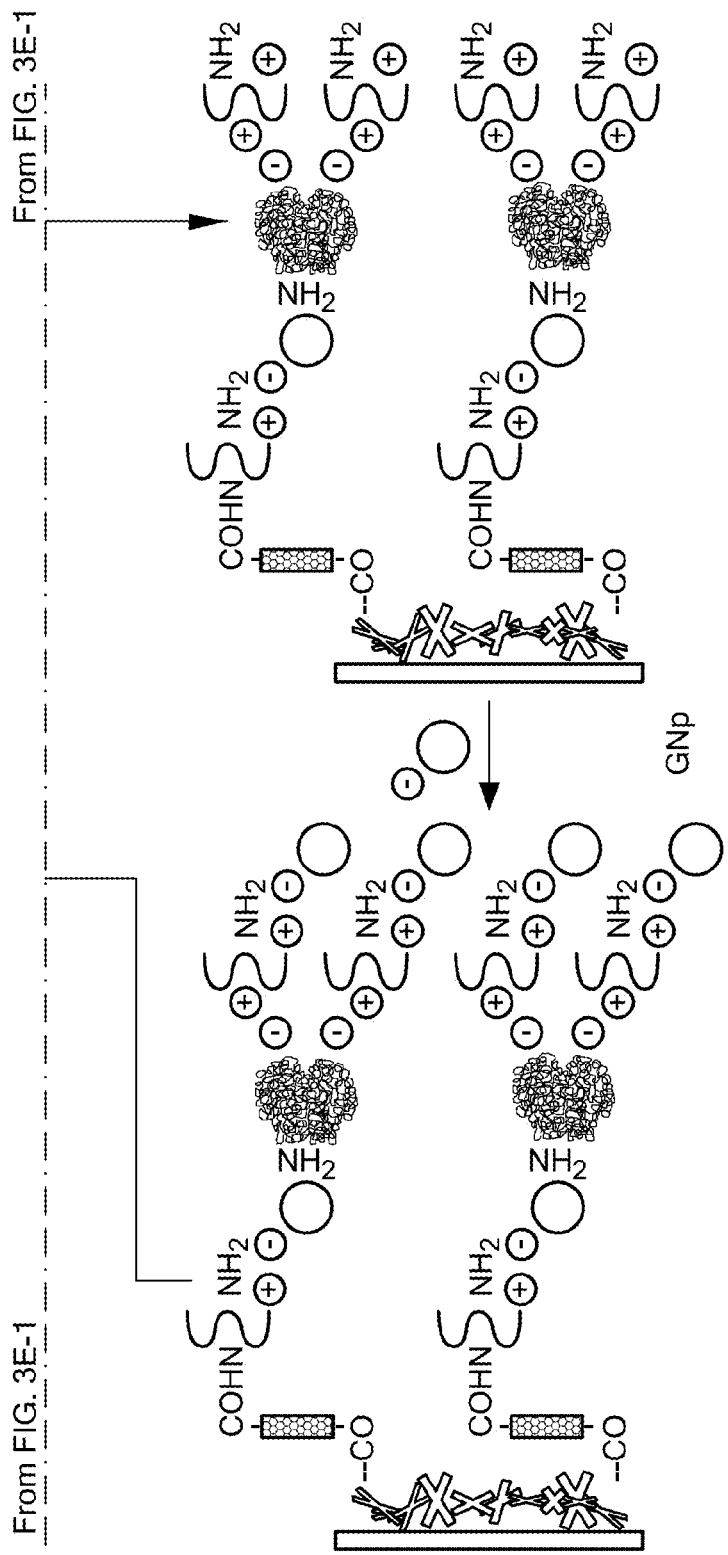
Figure 3F:
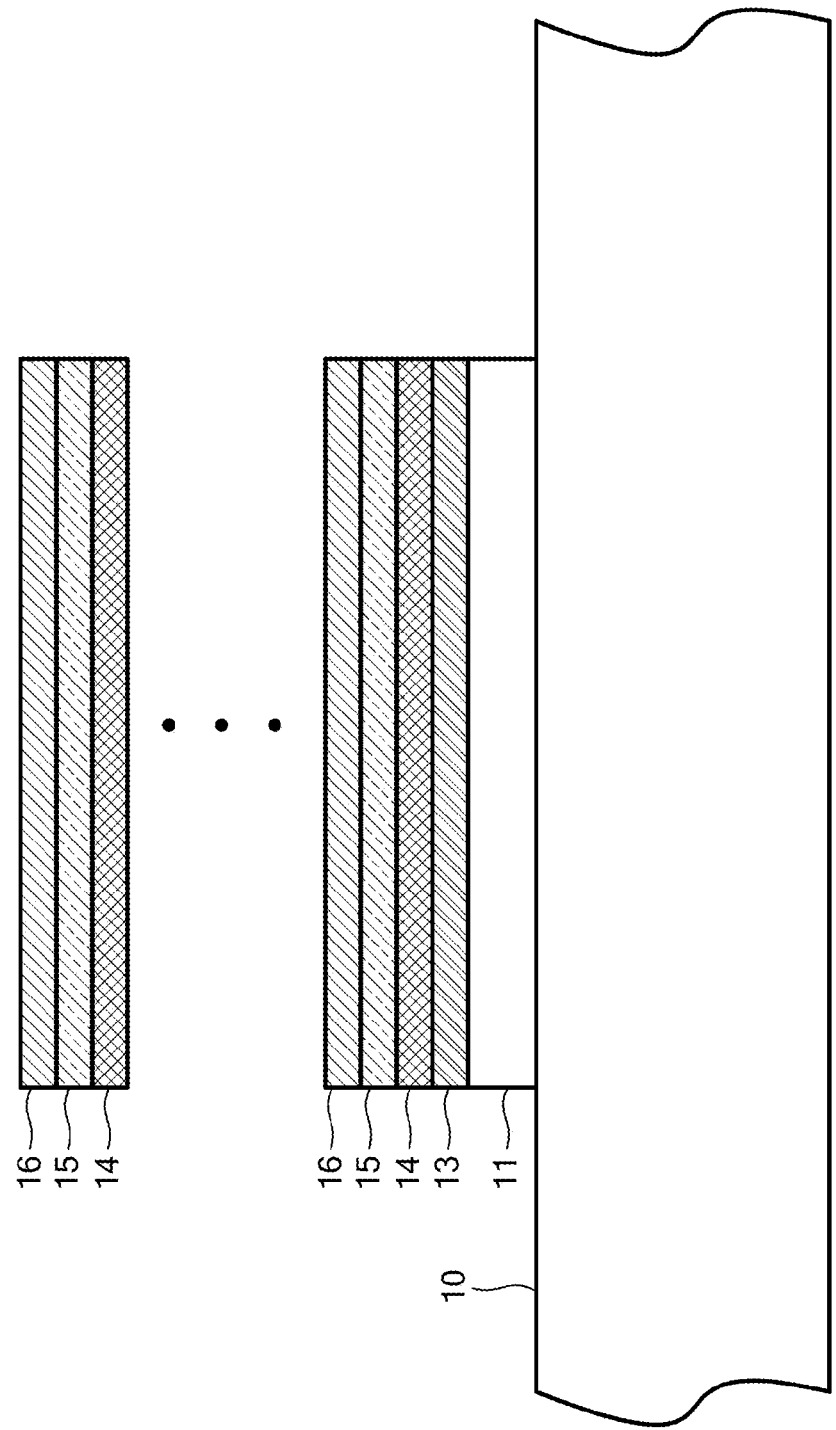
FIG. 3F shows a cross-section of the saliva glucose sensor as fabricated according to FIGS. 3E1 and 3E2. The layers of the sensor are indicated as follows: 10—insulating or semiconducting substrate (e.g., silicon or ceramic material); 11—conductive metal layer (e.g., platinum); 13—SWNT layer; 14—chitosan layer (CS); 15—gold nanoparticle layer (GNp); and 16—glucose oxidase layer (GOx).
Figure 3G:
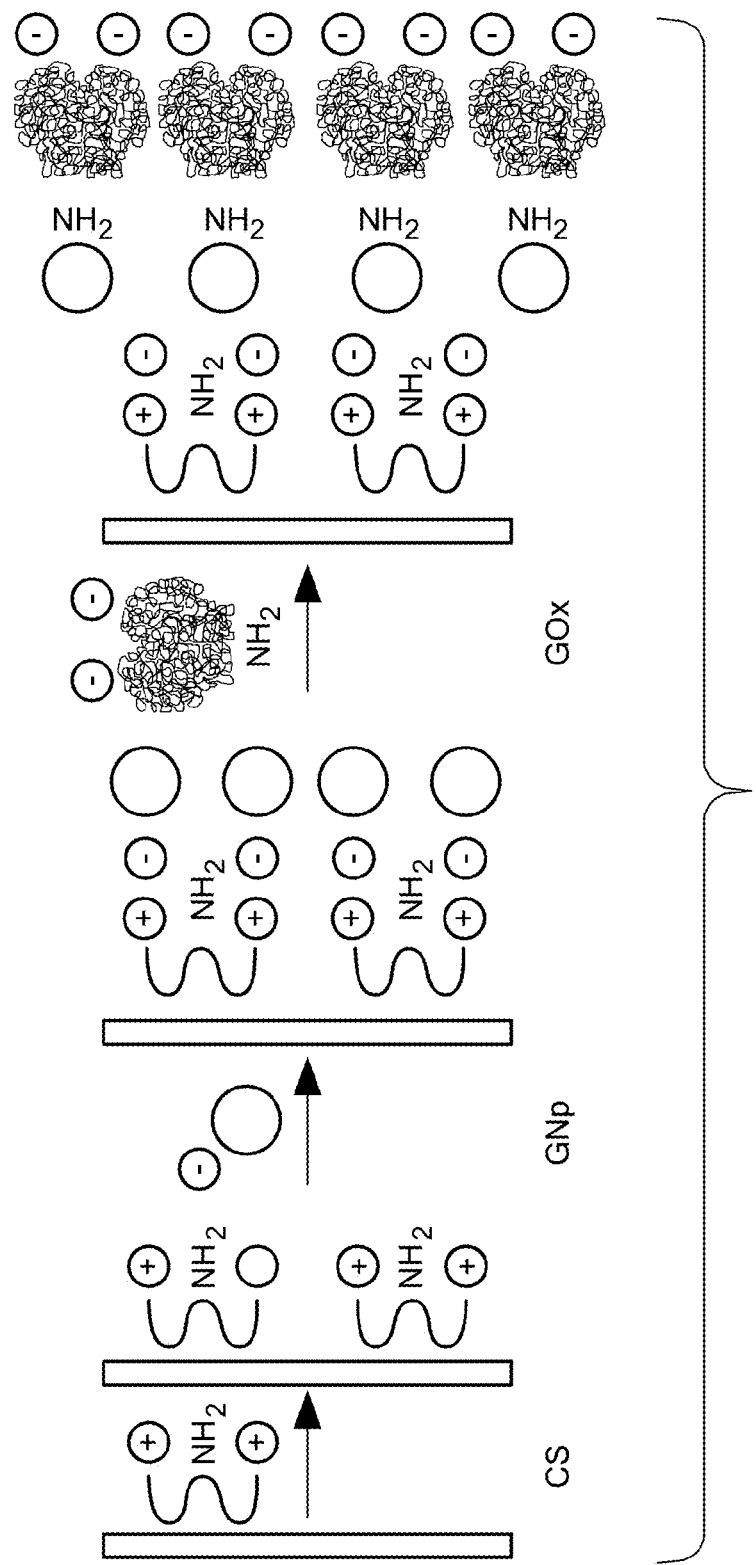
FIG. 3G shows a schematic representation of an embodiment of a process for functionalizing an electrode surface absent SWNT for glucose detection. Functionalization is accomplished by applying a coating using the bonding mechanism shown, wherein the coating does not include sensor elements (SWNT), and a coating containing chitosan, gold nanoparticles, and glucose oxidase is applied directly to the substrate.

Yet another embodiment of the assembly process involves the use of screen printing on the substrate. One such method is shown in FIGS. 3E and 3F. Such a method can optionally omit the SWNT layer, as shown in FIGS. 3G and 3H.

The electrodes of saliva glucose sensors can be easily fabricated, for example by electron-beam (E-beam) deposition or screen printing methods. One embodiment is to manufacture E-beam deposited sensors and apply layer-by-layer coating processes as described herein. The working electrode can be functionalized, for example, with one layer of SWNT and three layers of (GOx/GNp/CS) using the process as shown in FIG. 3A, or alternatively by the process shown in FIG. 3C. Another embodiment is to use screen-printed test strips and apply a layer-by-layer coating process as described herein. The working electrode can be functionalized, for example with one layer of SWNT and three layers of (GOx/GNp/CS) using a process as described in FIG. 3E.

A sensor system according to the invention can use either treated or untreated saliva or other fluid as the test sample. Saliva pretreatment can be achieved, for example, by passing a patient sample or another sample through a semi-permeable membrane that coats the sensor surface. Alternatively, for ease of use, a sensor system can be used which allows direct contact of the sensor element with saliva in the mouth. In yet another embodiment, the sensor system includes a built-in saliva filtration mechanism, which can be, for example, a microfluidics-based system. In certain embodiments, the sensor system serves as a glucose meter that includes a signal conditioner and a microcontroller; such a system can perform a series of amperometric measurements and display the glucose concentration from each measurement as an output signal or value, e.g., using a numerical display, graphic display, a dial indicator, or a color-based display indicating selected ranges or conditions. Optionally, the sensor system can compute and display an estimated equivalent blood glucose level corresponding to the measured saliva glucose level.

The above-described system can be implemented on a single chip, onto which a single drop of saliva can be applied as shown in FIG. 2b. The chip or sensor can be designed for single use (i.e., disposable) or for repeated use, with rinsing off or simple displacement of the saliva sample between readings. It can be used for real-time, noninvasive glucose monitoring for individuals at home and around clock. Through continuous or periodic glucose monitoring, additional temporal information can be obtained, such as trends, magnitude, duration, and frequency of certain glucose levels; this would allow tracking of data for better and more accurate assessment of a disease as well as the overall health condition of an individual. For example, the sensor system can activate an alarm for unusual or extreme glucose levels, decreasing the nursing workload when trying to maintain tight glycemic control. Such a system can also facilitate automatic feedback-controlled insulin delivery in an insulin delivery system, such as an artificial pancreas or insulin pump.

Figure 4:
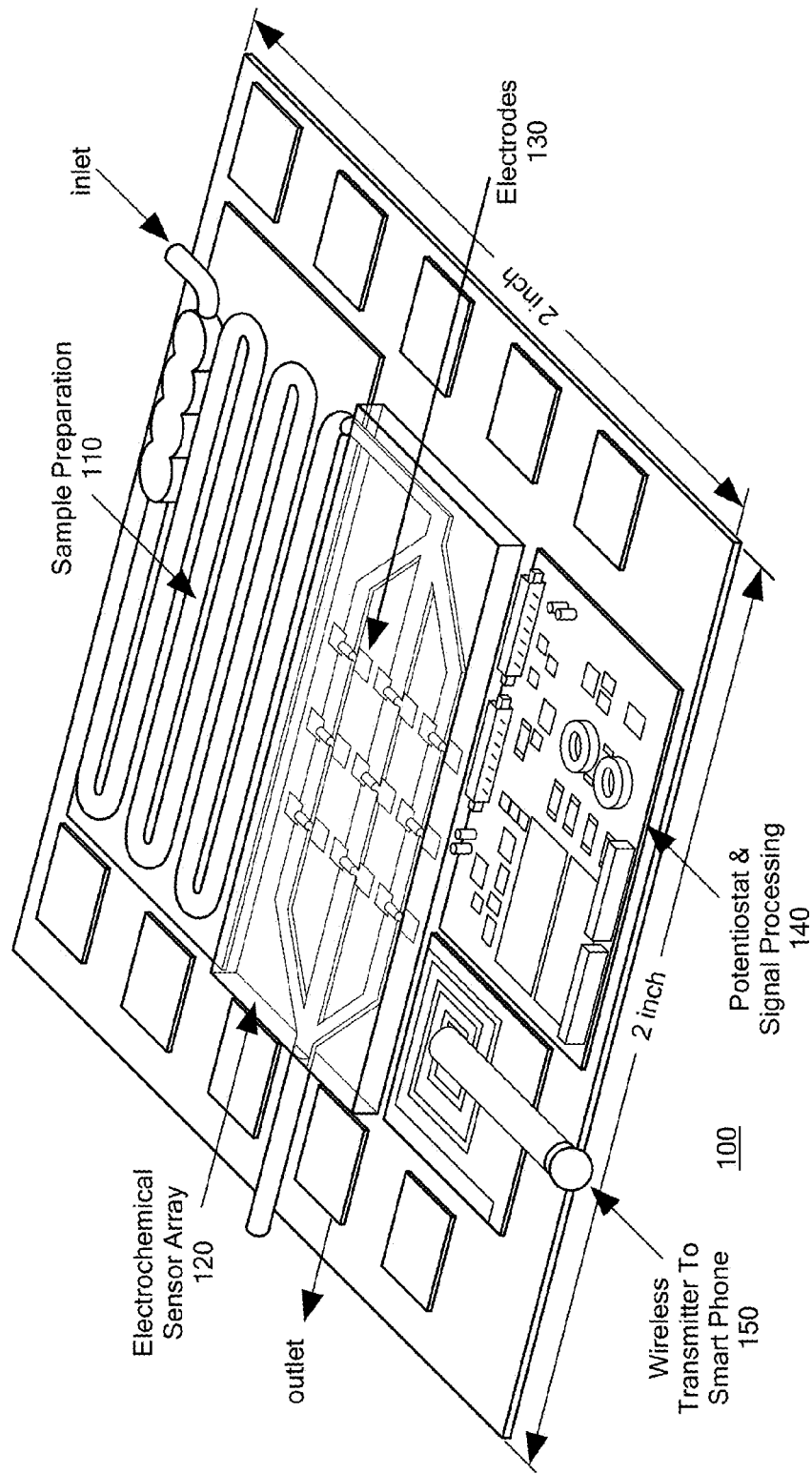
FIG. 4 shows a diagrammatic representation of a microfluidics embodiment of a glucose sensor of the invention.

In a microfluidics embodiment, the sensor system can utilize a small sample volume which is passed through one or more microfluidic channels. An example of such an embodiment is shown in FIG. 4. Saliva can pass through an optional sample preparation channel and arrive at a glucose sensor array in a detection chamber on the same microfluidics chip. This microfluidics-based sensor system can serve as a platform for detection or monitoring of a disease using saliva, blood, or other body fluids, or a combination of such fluids.

The sensor system of the invention has the following features: 1) High resolution. It can detect glucose levels down to 5 ppm (0.5 mg/dL) or lower. 2) It provides noninvasive measurement of glucose level without pricking the fingers. 3) It offers easy operation without pain. 4) It has a short response time of less than 10-20 seconds, yet offers accurate analysis. 5) It allows continuous glucose level monitoring for individuals, providing awareness of their health conditions. 6) It provides a simplified saliva sampling method. 7) The results show physiological trends which are comparable with blood glucose level determination. 8) The sensor or sensor system is portable and reusable. 9) It uses saliva for glucose detection. 10) The device can be configured as part of a platform for oral health monitoring and screening. 11) It allows accumulation of data through day to day measurements for additional temporal information, such as trends, magnitude, duration, and frequency of certain glucose levels. 12) It can be used to study diseases of the mouth using saliva samples by including suitable differential reactive chemistries substituted for glucose oxidase. 13) It can set alarm levels for detection of extreme and unusual glucose levels, which can decrease the nursing workload where tight glycemic control is required and facilitate automatic feedback-control for insulin delivery systems, such as an artificial pancreas or insulin pump.

The sensor can be miniaturized and optimized in size or configuration for the desired application. The sensitivity can be optimizing by adjusting the coating procedure of the working electrode and building a production line so as to achieve uniformity. The sensor can serve as a stand-alone device, or it can be incorporated into another device.

EXAMPLES

Example 1

Glucose Tolerance Test by Determination of Saliva Glucose Using Glucose Sensors Fabricated by E-Beam Deposition A study was performed on one healthy human subject to conduct saliva glucose monitoring for over 3-hour time period. The subject was asked to fast overnight and then asked to drink a glucose-containing beverage (75 g Trutol®) after fasting saliva samples were taken. The test simulated a glucose tolerance test. Five more saliva samples were taken at 15 min, 30 min, 60 min, 120 min, and 180 min intervals after consumption of the glucose containing beverage. Each saliva sample was measured at least three times with disposable saliva glucose sensors of the invention, and each blood sample, taken at the same times as the saliva samples, was measured at least three times with commercial disposable Freestyle blood test strips. The results are shown in FIG. 5A (saliva glucose measurements) and FIG. 5B (blood glucose measurements).

Figure 5A:
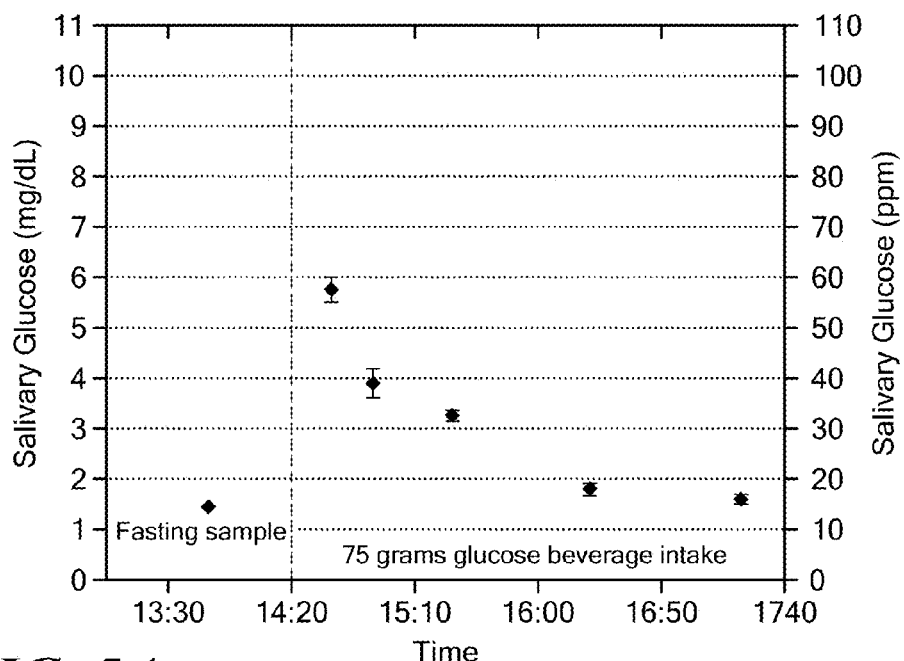
FIG. 5A shows glucose level monitoring using E-beam deposited saliva glucose sensors.
Figure 5B:
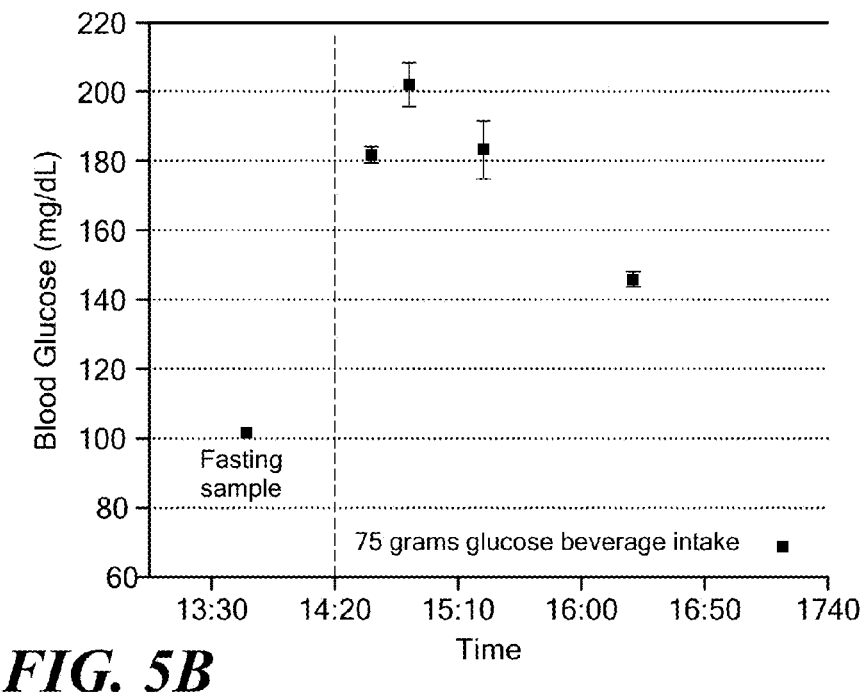
FIG. 5B shows glucose level monitoring using a Freestyle blood glucose meter. Values are shown for Subject A before and after intake of a glucose tolerance beverage at the indicated time.

The first point on the time axis represents the collected fasting sample, and the rest of the data points represent values determined after the intake of the glucose beverage, as shown in FIGS. 5A and 5B. The dashed line indicates the time of glucose beverage intake. The saliva glucose level reached a peak at around 15 min after the glucose beverage intake, then decreased and returned to normal in 2 hours. The blood glucose level reached a peak value at about 30 min after intake of the glucose beverage and dropped to normal about 2.5 hours later. The saliva glucose sensors of the invention were sensitive to expected physiological changes in saliva glucose, and the results obtained paralleled the results obtained by blood glucose determination.

Example 2

Glucose Tolerance Test by Determination of Saliva Glucose Using Glucose Sensors Fabricated by Screen Printing Another clinical trial was performed on three healthy human subjects to conduct saliva glucose monitoring over a 2-hour period with glucose challenge after fasting. The test was conducted similar to that described in Example 1, except that in this study screen-printed saliva glucose sensors according to the invention were used. The working electrode was functionalized with one layer of SWNT and three layers of (GOx/GNp/CS) using the process as described in FIG. 3C. The results were compared to blood glucose measurements.

The subjects were asked to fast overnight and to drink the glucose tolerance beverage after taken fasting saliva and blood samples. Four more set of saliva and blood samples from Subject B were measured at time intervals of 30 min, 45 min, 75 min, and 125 min (FIGS. 6A and 6B). and six more for Subjects C and D at time intervals of 15 min, 30 min, 45 min, 60 min, 90 min, and 120 min (FIGS. 7A, 7B, 8A, and 8B, respectively). Each saliva sample was measured at least three times with disposable saliva glucose sensors, and each blood sample was measured at least three times with commercial disposable Freestyle Lite blood test strips.

Figure 6A:
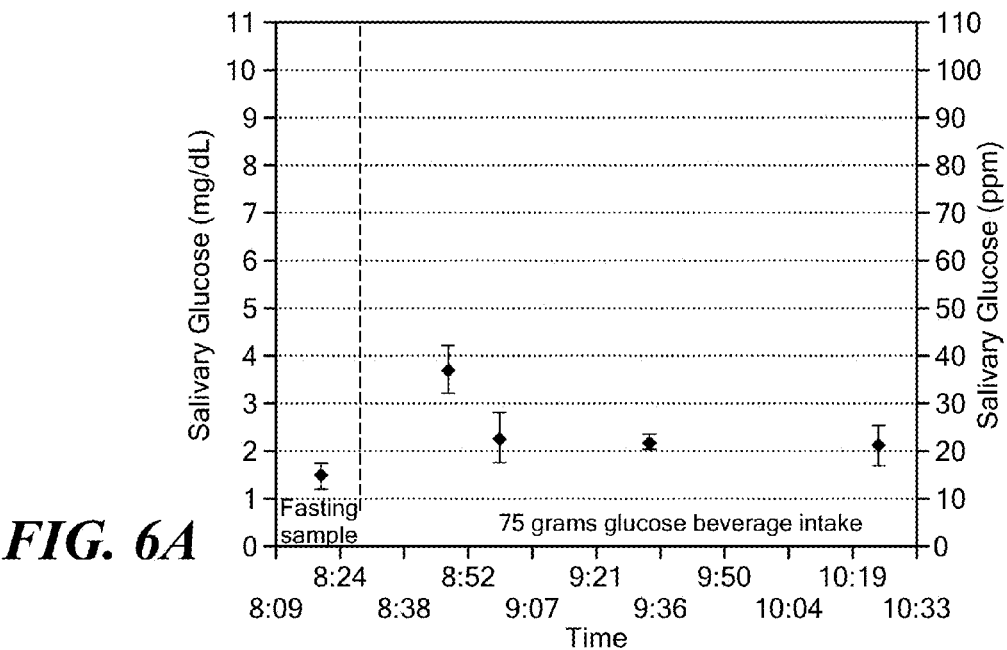
FIG. 6A shows glucose level monitoring using screen printed saliva glucose sensors.
Figure 6B:
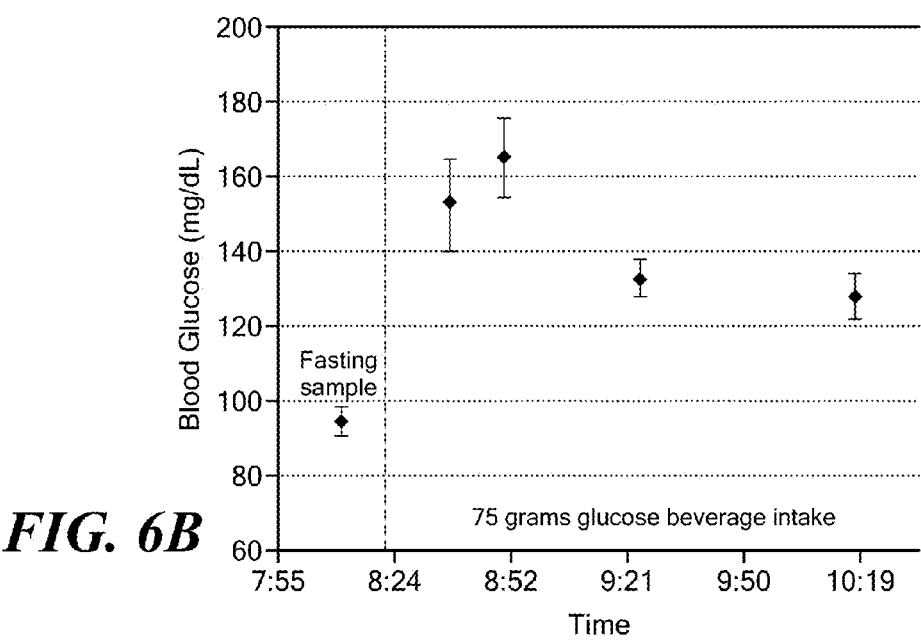
FIG. 6B shows glucose level monitoring using a Freestyle blood glucose meter. Values are shown for Subject B before and after intake of a glucose tolerance beverage at the indicated time.
Figure 7A:
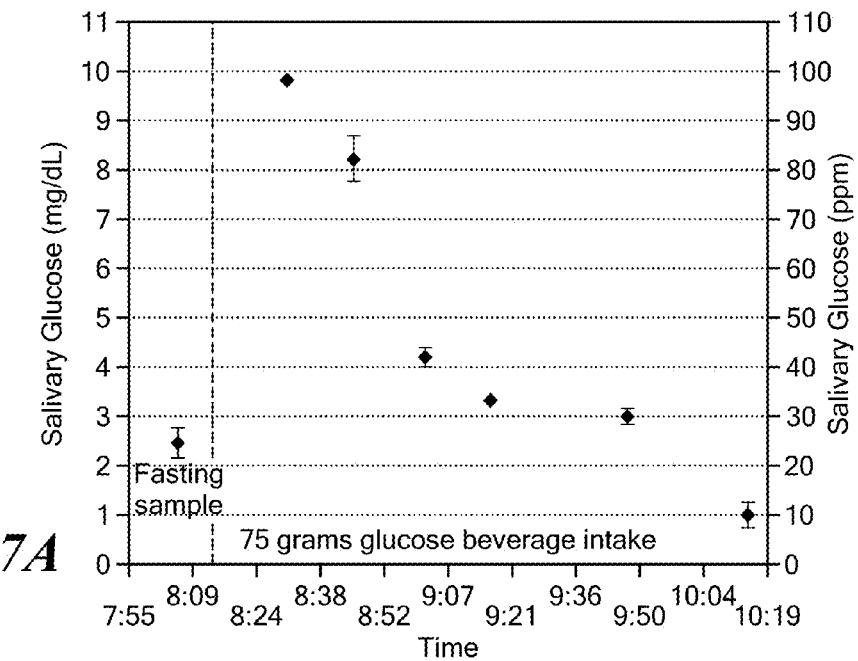
FIG. 7A shows glucose level monitoring using screen printed saliva glucose sensors.
Figure 7B:
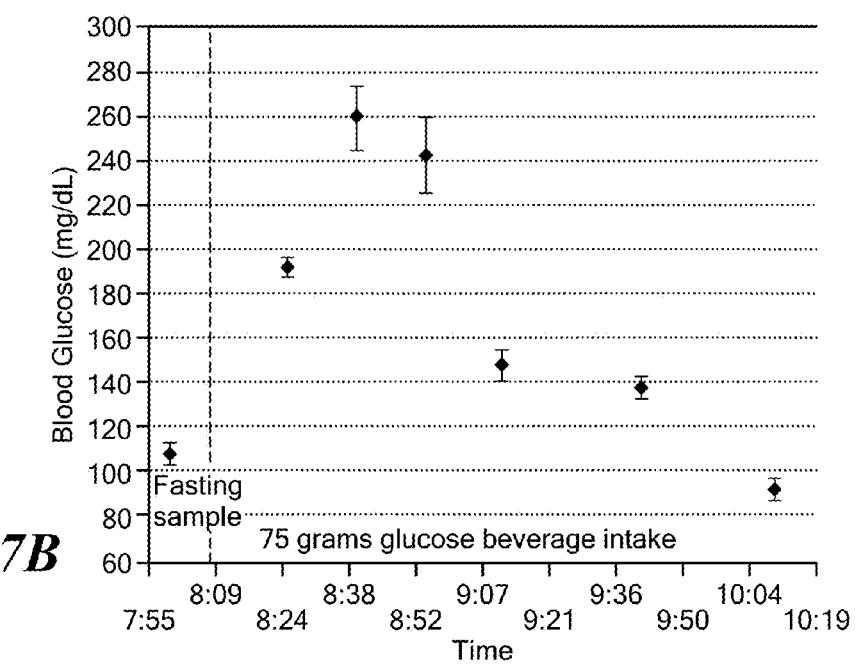
FIG. 7B shows glucose level monitoring using a Freestyle blood glucose meter. Values are shown for Subject C before and after intake of a glucose tolerance beverage at the indicated time.
Figure 8A:
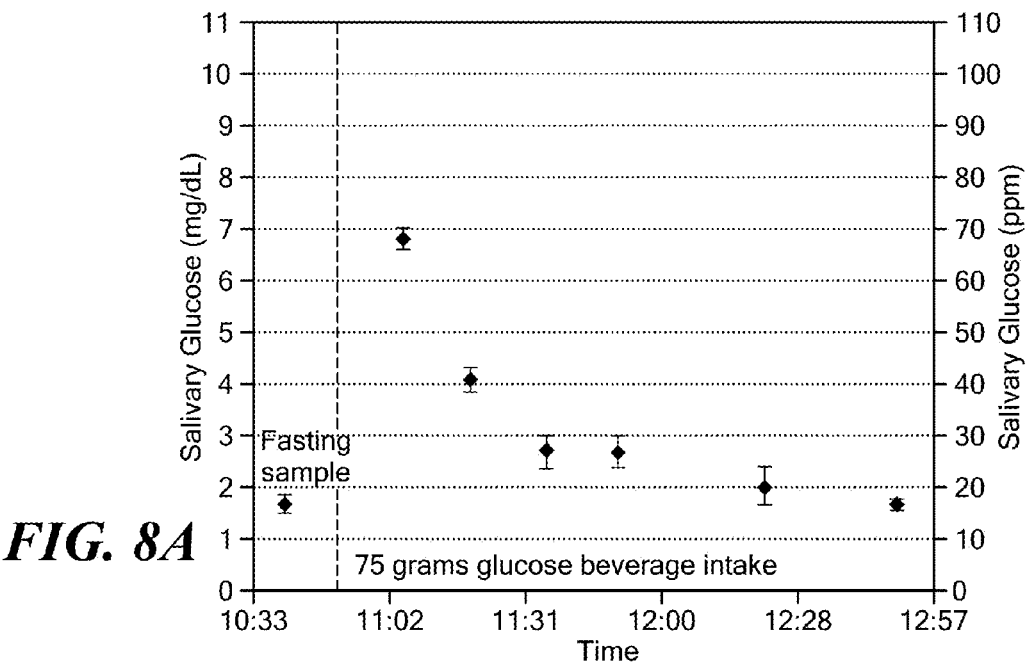
FIG. 8A shows glucose level monitoring using screen printed saliva glucose sensors.
Figure 8B:
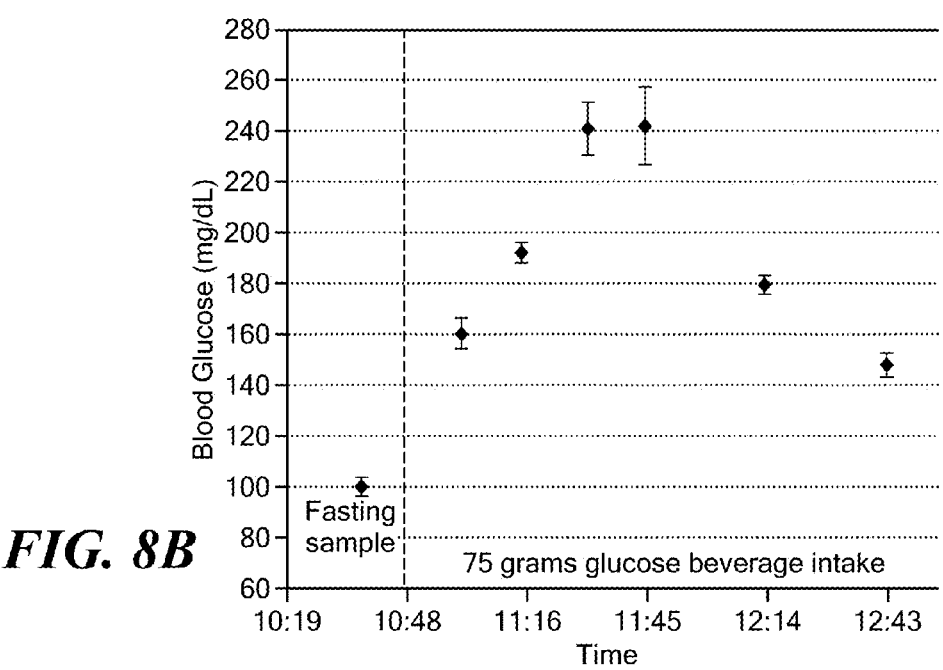
FIG. 8B shows glucose level monitoring using a Freestyle blood glucose meter. Values are shown for Subject D before and after intake of a glucose tolerance beverage at the indicated time.

The first point is the fasting sample and the rest are the samples after intake of the glucose beverage, as shown in FIGS. 6A, 7A, and 8A for saliva glucose and FIGS. 6B, 7B, and 8B for blood glucose. The dashed line indicates the time of glucose beverage intake. The subjects' saliva glucose levels all reached a peak within half an hour, then decreased, and almost returned to normal after 2 hours. Blood glucose levels reached peak values about 40 minutes after intake of glucose beverage and continued to drop over 2 hours.

These saliva glucose monitoring tests have successfully demonstrated that the saliva glucose monitoring system of the present invention can provide noninvasive, reliable (high resolution), convenient, fast, and continuous glucose level monitoring from saliva for personal use and point-of-care use.

As used herein, "consisting essentially of" allows the inclusion of materials or steps that do not materially affect the basic and novel characteristics of the claim, but excludes materials or steps that would materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

REFERENCES

[1]. World Health Organization. *Diabetes: Fact sheet N° 312*. Geneva (Switzerland): WHO; 2009. Available from: www.who.int/mediacentre/factsheets/fs312/en/. Accessed on Dec. 23, 2010.

[2]. Canadian Diabetes Association. Diabetes Progress Report 2005. Toronto (Ontario): Canadian Diabetes Association; 2005. Available from: www.diabetes.ca/files/diabetesreport2005/CDA-diabetesreport-2005-en.pdf.

[3]. Klonoff, D. C.; Perz, J. F., Assisted monitoring of blood glucose: special safety needs for a new paradigm in testing glucose. *J Diabetes Sci Technol* 2010, 4 (5), 1027-31.

[4]. Thompson, N. D.; Perz, J. F., Eliminating the blood: ongoing outbreaks of hepatitis B virus infection and the need for innovative glucose monitoring technologies. *J Diabetes Sci Technol* 2009, 3 (2), 283-8.

[5]. Thompson, N. D.; Schaefer, M. K., "Never events": hepatitis B outbreaks and patient notifications resulting from unsafe practices during assisted monitoring of blood glucose, 2009-2010. *J Diabetes Sci Technol* 2011, 5 (6), 1396-402.

[6]. Hayford, J. T.; Weydert, J. A.; Thompson, R. G., Validity of Urine Glucose Measurements for Estimating Plasma-Glucose Concentration. *Diabetes Care* 1983, 6 (1), 40-44.

[7]. Shen, Y. C.; Davies, A. G.; Linfield, E. H.; Elsey, T. S.; Taday, P. F.; Arnone, D. D., The use of Fourier-transform infrared spectroscopy for the quantitative determination of glucose concentration in whole blood. *Phys Med Biol* 2003, 48 (13), 2023-2032.

[8]. Burmeister, J. J.; Arnold, M. A.; Small, G. W., Noninvasive blood glucose measurements by near-infrared transmission spectroscopy across human tongues. *Diabetes Technol Ther* 2000, 2 (1), 5-16.

[9]. Nelson, L. A.; McCann, J. C.; Loepke, A. W.; Wu, J.; Ben Dor, B.; Kurth, C. D., Development and validation of a multiwavelength spatial domain near-infrared oximeter to detect cerebral hypoxia-ischemia. *J Biomed Opt* 2006, 11 (6), 064022.

[10]. Evans, N. D.; Gnudi, L.; Rolinski, O. J.; Birch, D. J.; Pickup, J. C., Non-invasive glucose monitoring by NAD(P)H autofluorescence spectroscopy in fibroblasts and adipocytes: a model for skin glucose sensing. *Diabetes Technol Ther* 2003, 5 (5), 807-16.

[11]. Katika, K. M.; Pilon, L., Feasibility analysis of an epidermal glucose sensor based on time-resolved fluorescence. *Appl Optics* 2007, 46 (16), 3359-3368.

[12]. Lambert, J. L.; Morookian, J. M.; Sirk, S. J.; Borchert, M. S., Measurement of aqueous glucose in a model anterior chamber using Raman spectroscopy. *Journal of Raman Spectroscopy* 2002, 33 (7), 524-529.

[13]. Enejder, A. M. K.; Scecina, T. G.; Oh, J.; Hunter, M.; Shih, W. C.; Sasic, S.; Horowitz, G. L.; Feld, M. S., Raman spectroscopy for noninvasive glucose measurements. *J Biomed Opt* 2005, 10 (3).

[14]. Rabinovitch, B.; March, W. F.; Adams, R. L., Noninvasive glucose monitoring of the aqueous humor of the eye: Part I. Measurement of very small optical rotations. *Diabetes Care* 1982, 5 (3), 254-8.

[15]. March, W. F.; Rabinovitch, B.; Adams, R. L., Noninvasive glucose monitoring of the aqueous humor of the eye: Part II. Animal studies and the scleral lens. *Diabetes Care* 1982, 5 (3), 259-65.

[16]. Cote, G. L.; Fox, M. D.; Northrop, R. B., Noninvasive Optical Polarimetric Glucose Sensing Using a True Phase Measurement Technique. *Ieee T Bio-Med Eng* 1992, 39 (7), 752-756.

[17]. King, T. W.; Cote, G. L.; Mcnichols, R.; Goetz, M. J., Multispectral Polarimetric Glucose Detection Using a Single Pockels Cell. *Opt Eng* 1994, 33 (8), 2746-2753.

[18]. MacKenzie, H. A.; Ashton, H. S.; Spiers, S.; Shen, Y.; Freeborn, S. E.; Hannigan, J.; Lindberg, J.; Rae, P., Advances in photoacoustic noninvasive glucose testing (vol 45, pg 1587, 1999). *Clin Chem* 1999, 45 (12), 2299-2299.

[19]. Aslan, K.; Lakowicz, J. R.; Szmacinski, H.; Geddes, C. D., Metal-enhanced fluorescence solution-based sensing platform. *J Fluoresc* 2004, 14 (6), 677-679.

[20]. Amarie, D.; Alileche, A.; Dragnea, B.; Glazier, J. A., Microfluidic Devices Integrating Microcavity Surface-Plasmon-Resonance Sensors: Glucose Oxidase Binding-Activity Detection. *Analytical Chemistry* 2010, 82 (1), 343-352.

[21]. Amir, O.; Weinstein, D.; Zilberman, S.; Less, M.; Perl-Treves, D.; Primack, H.; Weinstein, A.; Gabis, E.; Fikhte, B.; Karasik, A., Continuous noninvasive glucose monitoring technology based on "occlusion spectroscopy". *J Diabetes Sci Technol* 2007, 1 (4), 463-9.

[22]. Jurysta, C.; Bulur, N.; Oguzhan, B.; Satman, I.; Yilmaz, T. M.; Malaisse, W. J.; Sener, A., Salivary Glucose Concentration and Excretion in Normal and Diabetic Subjects. *J Biomed Biotechnol* 2009.

[23]. Mitsumori, M.; Yamaguchi, M.; Kano, Y., A new approach to noninvasive measurement of blood glucose using saliva analyzing system. *P Ann Int Ieee Embs* 1998, 20, 1767-1770.

[24]. Soares, M. S.; Batista-Filho, M. M.; Pimentel, M. J.; Passos, I. A.; Chimenos-Kustner, E., Determination of salivary glucose in healthy adults. *Med Oral Patol Oral Cir Bucal* 2009, 14 (10), e510-3.

[25]. Yamaguchi, M.; Mitsumori, M.; Kano, Y., Noninvasively measuring blood glucose using saliva. *Ieee Eng Med Biol* 1998, 17 (3), 59-63.

[26]. Amer, S.; Yousuf, M.; Siddqiui, P. Q.; Alam, J., Salivary glucose concentrations in patients with diabetes mellitus—a minimally invasive technique for monitoring blood glucose levels. *Pak J Pharm Sci* 2001, 14 (1), 33-7.

[27]. Vasconcelos, A. C.; Soares, M. S.; Almeida, P. C.; Soares, T. C., Comparative study of the concentration of salivary and blood glucose in type 2 diabetic patients. *J Oral Sci* 2010, 52 (2), 293-8.

[28]. Aren, G.; Sepet, E.; Ozdemir, D.; Dinccag, N.; Guvener, B.; Firatli, E., Periodontal health, salivary status, and metabolic control in children with type 1 diabetes mellitus. *J Periodontol* 2003, 74 (12), 1789-1795.

[29]. Aydin, S., A comparison of ghrelin, glucose, alpha-amylase and protein levels in saliva from diabetics. *J Biochem Mol Biol* 2007, 40 (1), 29-35.

[30]. Zeng, Z. Y.; Zhou, X. Z.; Huang, X. A.; Wang, Z. J.; Yang, Y. L.; Zhang, Q. C.; Boey, F.; Zhang, H., Electrochemical deposition of Pt nanoparticles on carbon nanotube patterns for glucose detection. *Analyst* 2010, 135 (7), 1726-1730.

[31]. Yan, X. B.; Chen, X. J.; Tay, B. K.; Khor, K. A., Transparent and flexible glucose biosensor via layer-by-layer assembly of multi-wall carbon nanotubes and glucose oxidase. *Electrochem Commun* 2007, 9 (6), 1269-1275.

[32]. Wu, B. Y.; Hou, S. H.; Yin, F.; Li, J.; Zhao, Z. X.; Huang, J. D.; Chen, Q., Amperometric glucose biosensor based on layer-by-layer assembly of multilayer films composed of chitosan, gold nanoparticles and glucose oxidase modified Pt electrode. *Biosens Bioelectron* 2007, 22 (6), 838-844.

[33]. Dimcheva, N.; Horozova, E.; Jordanova, Z., A glucose oxidase immobilized electrode based on modified graphite. *Z Naturforsch C* 2002, 57(7-8), 705-711.

[34]. Jia, J. Y.; Guan, W. J.; Sim, M. H.; Li, Y. Q.; Li, H., Carbon nanotubes based glucose needle-type biosensor. *Sensors* 2008, 8 (3), 1712-1718.

[35]. Claussen, J. C.; Kumar, A.; Jaroch, D. B.; Khawaja, M. H.; Hibbard, A. B.; Porterfield, D. M.; Fisher, T. S., Nanostructuring Platinum Nanoparticles on Multilayered Graphene Petal Nanosheets for Electrochemical Biosensing. *Advanced Functional Materials* 2012, 22 (16), 3399-3405.

[36]. Wang, H. C.; Wang, X. S.; Zhang, X. Q.; Qin, X.; Zhao, Z. X.; Miao, Z. Y.; Huang, N.; Chen, Q., A novel glucose biosensor based on the immobilization of glucose oxidase onto gold nanoparticles-modified Pb nanowires. *Biosens Bioelectron* 2009, 25 (1), 142-146.

[37]. Zhuang, Z. J.; Su, X. D.; Yuan, H. Y.; Sun, Q.; Xiao, D.; Choi, M. M. F., An improved sensitivity non-enzymatic glucose sensor based on a CuO nanowire modified Cu electrode. *Analyst* 2008, 133 (1), 126-132.

[38]. Wang, Y.; Wei, W. Z.; Liu, X. Y.; Zeng, X. D., Carbon nanotube/chitosan/gold nanoparticles-based glucose biosensor prepared by a layer-by-layer technique. *Mat Sci Eng C-Bio S* 2009, 29 (1), 50-54.

[39]. Zhu, J. H.; Zhu, Z. Q.; Lai, Z. S.; Wang, R.; Guo, X. M.; Wu, X. Q.; Zhang, G. X.; Zhang, Z. R.; Zhang, Z. R.; Wang, Y. T.; Chen, Z. Y., Planar amperometric glucose sensor based on glucose oxidase immobilized by chitosan film on Prussian blue layer. *Sensors* 2002, 2 (4), 127-136.

[40]. Li, L.; Sheng, Q. L.; Zheng, J. B.; Zhang, H. F., Facile and controllable preparation of glucose biosensor based on Prussian blue nanoparticles hybrid composites. *Bioelectrochemistry* 2008, 74 (1), 170-175.

[41]. Hoshi, T.; Saiki, H.; Kuwazawa, S.; Tsuchiya, C.; Chen, Q.; Anzai, J., Selective permeation of hydrogen peroxide through polyelectrolyte multilayer films and its use for amperometric biosensors. *Analytical Chemistry* 2001, 73 (21), 5310-5315.

[42]. Huang, H. Z.; Yang, X. R., Chitosan mediated assembly of gold nanoparticles multilayer. *Colloid Surface A* 2003, 226 (1-3), 77-86.

[43]. Luo, X. L.; Xu, J. J.; Zhang, Q.; Yang, G. J.; Chen, H. Y., Electrochemically deposited chitosan hydrogel for horseradish peroxidase immobilization through gold nanoparticles self-assembly. *Biosens Bioelectron* 2005, 21 (1), 190-196.

[44]. Yu, L.; Ming, W.; M. Dokmeci.; Wireless SWNT Sensor Integrated with Micro fluidic System for Various Liquid Sensing Applications. Provisional Patent 61/584,857.

The invention claimed is:

1. A glucose sensor for determining a concentration of glucose in a liquid sample, the sensor comprising:
    an insulating or semiconducting substrate;
    at least one working electrode, a counter electrode, and a reference electrode, and
    a sample placement area on a surface of the substrate for containing the liquid sample during a determination of the glucose concentration in the liquid sample;
    wherein each of the working electrode(s), counter electrode, and reference electrode comprises a conductive metal layer deposited on the substrate in the sample placement area; wherein the working electrode is coated in the sample placement area with a plurality of sensor elements; wherein the sensor elements in the sample placement area are functionalized with a functionalization coating comprising from 2 to 10 layers, each layer comprising a sublayer of chitosan, a sublayer of gold nanoparticles deposited onto the chitosan, and a sublayer of glucose oxidase deposited onto the gold nanoparticles; wherein the working electrode, counter electrode, and reference electrode are connected to an amperometry circuit; wherein the sensor measures electron transfer through the glucose oxidase into the working electrode; and wherein an output voltage of the amperometry circuit correlates with a glucose concentration in the liquid sample deposited in the sample placement area.

2. The glucose sensor of claim 1, wherein the substrate comprises a material selected from the group consisting of silicon, glass, ceramic, a non-conductive polymer, and combinations thereof.

3. The glucose sensor of claim 1, wherein the working electrode comprises one or more materials selected from the group consisting of gold, platinum, iridium, silver, silver/silver chloride, and combinations thereof.

4. The glucose sensor of claim 1, wherein the sensor elements comprise a material selected from the group consisting of single-walled carbon nanotubes (SWNT), graphite, graphene, carbon nanofibers, carbon nanowires, and combinations thereof.

5. The glucose sensor of claim 1, further comprising a layer comprising a polycationic polymer disposed on the conductive metal layer of the working electrode and beneath the sensor elements, and beneath the functionalization coating.

6. The glucose sensor of claim 5, wherein the polycationic polymer is selected from the group consisting of polyallylamine, poly(L-lysine), polyethyleneimine, polyamidoamine dendrimers, and combinations thereof.

7. The glucose sensor of claim 1, wherein the sensor element functionalization coating further comprises one or more materials selected from the group consisting of graphite, graphene, platinum nanoparticles, serum albumin, and Prussian Blue.

8. The glucose sensor of claim 1, further comprising a sensor element protective membrane.

9. The glucose sensor of claim 8, wherein the sensor element protective membrane comprises Nafion, a lipid bilayer, or another semi-permeable membrane.

10. The glucose sensor of claim 1 that is a component of a microfluidics device, wherein the microfluidics device comprises one or more channels that deliver a liquid sample to the sample placement area.

11. The glucose sensor of claim 1 that is capable of detecting glucose at concentrations down to 5 ppm (0.5 mg/dL) or lower.

12. The glucose sensor of claim 1 that is configured as a disposable device or a reusable device.

13. The glucose sensor of claim 1 that is configured for determination of glucose concentration in saliva.

14. The glucose sensor of claim 1 comprising one or more working electrodes having functionalized sensor elements capable of detecting an analyte other than glucose.

15. A method of determining a glucose concentration in a liquid sample, the method comprising the steps of:
(a) providing the glucose sensor of claim 1;
(b) introducing a liquid sample into the sample placement area of the sensor; and
(c) determining the glucose concentration in the liquid sample from an electrical output of the sensor.

16. The method of claim 15 further comprising the steps of:
(d) removing the liquid sample introduced in step (b);
(e) introducing a new liquid sample into the sample placement area of the sensor; and
(f) determining a new glucose concentration in the new liquid sample from an electrical output of the sensor.

17. The method of claim 15, wherein the liquid sample is from a subject who has diabetes, is suspected of having diabetes, or is healthy.

18. The method of claim 15, wherein the liquid sample is a saliva sample.

\* \* \* \* \*